US010995352B2

(12) United States Patent
Nandi et al.

(10) Patent No.: US 10,995,352 B2
(45) Date of Patent: May 4, 2021

(54) GLYCOLIPID COMPOSITION AND METHOD THEREOF

(71) Applicant: ExxonMobil Research and Engineering Company, Annandale, NJ (US)

(72) Inventors: Partha Nandi, Annandale, NJ (US); Xiaozhou Zhang, Bridgewater, NJ (US); Mohor Chatterjee, Annandale, NJ (US); Vera Grankina, Union Dale, PA (US); Changyub Paek, Bridgewater, NJ (US); Fang Cao, Basking Ridge, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 16/870,910

(22) Filed: May 9, 2020

(65) Prior Publication Data

US 2020/0377916 A1 Dec. 3, 2020

Related U.S. Application Data

(60) Provisional application No. 62/856,450, filed on Jun. 3, 2019.

(51) Int. Cl.
*C12P 19/12* (2006.01)
*C12P 7/06* (2006.01)
(Continued)

(52) U.S. Cl.
CPC .............. *C12P 19/12* (2013.01); *C12N 1/16* (2013.01); *C12P 5/026* (2013.01); *C12P 7/06* (2013.01); *C12P 7/16* (2013.01)

(58) Field of Classification Search
CPC ......... A61P 31/04; A61P 35/00; A61P 25/16; A61P 37/08; A61P 9/00; A61P 31/00; A61P 31/12; A61P 37/02; A61P 11/08; A61P 13/02; A61P 15/00; A61P 1/08; A61P 21/00; A61P 21/02; A61P 23/00; A61P 25/06; A61P 25/08; A61P 25/20; A61P 27/20; A61P 29/00; A61P 33/00; A61P 33/06; A61P 3/02; A61P 3/08; A61P 3/10; A61P 3/14; A61P 5/00; A61P 7/10; A61P 9/12; A61P 19/02; A61P 25/28; A61P 31/10; A61P 31/18; A61P 33/02; A61P 37/06; A61P 17/00; A61P 37/00; A61P 37/04; A61P 1/16; A61P 17/02; A61P 25/00; A61P 25/14; A61P 25/18; A61P 27/02; A61P 39/02; A61P 3/00; A61P 43/00; A61P 31/16; A61P 3/12; A61K 2039/53; A61K 2039/55566; A61K 9/107; A61K 38/38; A61K 38/40; A61K 9/0043; A61K 9/006; A61K 31/713; A61K 39/12; A61K 39/155; A61K 9/0019; A61K 39/385; A61K 39/39; A61K 31/706; A61K 31/7072; A61K 31/443; A61K 31/661; A61K 31/665; A61K 31/7052; A61K 31/664; A61K 31/716; A61K 45/00; A61K 45/06; A61K 9/20; A61K 31/7076; A61K 31/708; A61K 31/7084; C12N 2760/18534; C12N 1/16; C12N 1/26; Y02A 50/30; Y02A 50/412; Y02A 50/489; Y02A 20/55; C11D 1/00; C11D 1/146; C11D 1/22; C11D 1/28; C11D 1/29; C11D 1/37; C11D 1/62; C11D 1/645; C11D 1/662; C11D 1/667; C11D 1/72; C11D 1/75; C11D 1/83; C11D 1/86; C11D 1/92; C11D 1/94;
(Continued)

(56) References Cited

U.S. PATENT DOCUMENTS 9,683,164 B2 6/2017 Gunawan et al.
2015/0300139 A1 10/2015 Armstrong et al.
(Continued)

FOREIGN PATENT DOCUMENTS

EP 0550280 B1 6/1996
EP 1411111 B1 9/2008
EP 3330341 A1 6/2018

OTHER PUBLICATIONS

Abdul Samed et al, "Sweet sorghum bagasse and corn stover serving as substrates for producing sophorolipids", J. Ind. Microbiol Biotechnol (2017) 44:353-362,. (Year: 2017).*
(Continued)

*Primary Examiner* — Deborah K Ware
(74) *Attorney, Agent, or Firm* — Kristina Okafor

(57) ABSTRACT

The present disclosure relates to glycolipid compositions, methods for making glycolipid compositions, and their uses thereof. Glycolipid compositions can be prepared via yeast-mediated catalyzed reaction, and exhibit excellent surfactant properties having high corrosion inhibition performance, good reducing surface tension efficiency. Processes of the present disclosure can provide glycolipid compositions having one or more of: a ratio of lactonic glycolipids to glycolipid acylic esters is from about 1:10 to about 10:1, a molecular weight of from about 400 g/mol to about 10,000 g/mol, a corrosion rate of carbon steel from about 0.5 MPY to about 100 MPY at room temperature and at pH 4-6. Furthermore, aqueous solutions of the glycolipid compositions of the present disclosure can have a surface tension of from about 20 mN/m to about 80 mN/m.

9 Claims, 10 Drawing Sheets

(51) Int. Cl.
*C12N 1/16* (2006.01)
*C12P 5/02* (2006.01)
*C12P 7/16* (2006.01)

(58) Field of Classification Search
CPC .... C07H 19/207; C07H 23/00; C07H 19/044; C07H 19/052; C07H 19/20; C07H 19/10; C07H 19/04; C07H 11/04; C07H 19/048; C07H 17/02; C07H 19/06; C07H 1/00; C07H 19/24; C07H 15/10; Y02E 50/10; Y02E 50/30; Y10T 428/105; C07F 9/65586; C07F 9/65742; C07F 9/06; C07F 9/242; C07F 9/547; C07F 9/6561; C07F 9/24; C07F 9/2479; C07F 7/1804; C07F 9/2458; C07F 9/65517; C07F 9/65616; C07F 9/65515; C08G 63/06; C08G 63/89; C07B 2200/13; C12P 19/12; C12P 5/026; C12P 7/06; C12P 7/16; C12P 19/44; C07D 307/33; C07D 317/30; C07D 413/06; C09K 19/12; C09K 19/3003; C09K 2019/123; C09K 2019/124; C09K 2019/3025; C09K 2323/035; G02B 5/3016; G02B 5/3083

See application file for complete search history.

(56) References Cited

U.S. PATENT DOCUMENTS

| | | | |
|---|---|---|---|
| 2015/0336999 A1 | 11/2015 | Jourdier et al. | |
| 2016/0237334 A1 | 8/2016 | Gunawan et al. | |
| 2017/0183702 A1* | 6/2017 | Boundy-Mills | C07H 15/06 |

OTHER PUBLICATIONS

Morya et al , "Production and characterization of low molecular weight sophorolipid underfed-batch culture", Bioresource Technology, 143 (2013)pp. 282-288. (Year: 2013).*

Exhibit A, "Fatty acid molecular weights.", Adapted from A.J. Sheppard, Lipid Manual , US FDA, 1992, and copyrighted by Anders Meller, Danish Food Information, 2011. (Year: 2011).*

N. Baccile, et al "Development of a Cradle-to-Grave Approach for Acetylated Acidic Sophorolipid Biosurfactants" ACS Sustainable Chemistry & Engineering, 2017, 5, pp. 1186-1198.

E.I.P. Delbeke, et al. "Chapter 14—Sophorolipid Modification: The Power of Yeasts and Enzymes" Lipid Modification by Enzymes and Engineered Microbes, Edited by Bornscheuer UT: AOCS Press, 2018, pp. 315-341.

I.N.A. Van Bogaert, et al. "Microbial synthesis of sophorolipids" Process Biochemistry, 2011, 46, pp. 821-833.

I.N.A. Van Bogaert, et al. "Microbial production and application of sophorolipids" Applied Microbiology and Biotechnology, 2007, 76, pp. 23-34.

H., Wang, et al. "Starmerella bombicola: recent advances on sophorolipid production and prospects of waste stream utilization" J. Chem. Technol. Biotechnol., 2019, 94, pp. 999-1007.

P. Ratsep, et al. "Identification and quantification of sophorolipid analogs using ultra-fast liquid chromatography—mass spectrometry" Journal of Microbiological Methods, 2009, 78, pp. 354-356.

J. D. Desai, et al. "Microbial Production of Surfactants and Their Commercial Potential" Microbiol. Bio. Rev., 1997, 61, pp. 47-64.

K. Ciesielskaa,et al. "Exoproteome analysis of Starmerella bombicola results in the discovery of an esterase required for lactonization of sophorolipids" Journal of Proteomics, 2014, 98, pp. 159-174.

Saerens, et al. "One-Step Production of Unacetylated Sophorolipids by an Acetyltransferase Negative Candida bombicola" Biotechnology and Bioengineering, 2011, vol. 108, No. 12.

A. Koh, et al. "Effect of Sophorolipid n Alkyl Ester Chain Length on Its Interfacial Properties at the Almond Oil-Water Interface" Langmuir, 2016, 32, pp. 5562-5572.

K. Hisatsuka, et al. "Formation of Protein-like Activator for n-Alkane Oxidation and Its Properties" Agric. Biol. Chem., 1977, 41 (3), pp. 445-450.

S. Inoue, et al. "Sophorolipids from Torulopsis bombicola as microbial surfactants in alkane fermentation" Biotechnology Letters, 1982, 4, pp. 3-8.

J. Rau, et al. "Sophorolipids: a Source for Novel Compounds" Industrial Crops and Products, 2001, 13, pp. 85-92.

L. Zhang, et al. "Synthesis and interfacial properties of sophorolipid derivatives" Colloids and Surfaces A: Physicochem. Eng. Aspects, 2004, 240, pp. 75-82.

W. Gao, et al. "Glycolipid Polymer Synthesized from Natural Lactonic Sophorolipids by Ring Opening Metathesis Polymerization" Macromolecules, 2007, 40 (2), pp. 145-147.

* cited by examiner

GLYCOLIPID COMPOSITION AND METHOD THEREOF

CROSS-REFERENCE TO RELATED APPLICATIONS

This application claims priority to U.S. Provisional Application No. 62/856,450 filed Jun. 3, 2019, which is herein incorporated by reference in its entirety.

FIELD OF THE INVENTION

The present disclosure relates to glycolipid compositions, methods for making compositions, and uses thereof. Particularly, the present disclosure relates to sophorolipid compositions, methods for making compositions, and uses thereof.

BACKGROUND OF THE INVENTION

Current market-trends show the global fast growing demand of bio-surfactants based on their utility in detergent, paint, cosmetics, textile, agriculture, food, and pharmaceutical industries. Microorganisms (yeasts, bacteria and some filamentous fungi) are capable of producing bio-surfactants with different molecular structures and surface activities. Glycolipids are one of the most important classes of bio-surfactants, as they possess excellent surface lowering properties. Glycolipids have a wide range of applications in the oil and gas industry, owing to their unique properties such as higher biodegradability and lower toxicity, when compared to their chemically synthesized counterparts. Accordingly, glycolipids have gained importance in the fields of enhanced oil recovery, corrosion inhibitor, bioremediation, oil mobilization, oil well treatment, fracturing subterranean formations, and engine lubricants. However, large-scale production of glycolipids has not been realized because of low yields in production processes and high recovery and purification costs.

Glycolipid bio-surfactants are used as corrosion inhibitors to control bio-corrosion of carbon steel caused by microorganisms, which is a considerable problem for the oil and gas industry, as it is considered as one of the most damaging mechanisms to pipeline steel materials. Furthermore, environmental regulations have prompted new challenges in the search for green corrosion inhibitors that are biodegradable and do not contain heavy metals.

Surfactants play a number of critical roles in lubrication, and are consequently important in lubricant formulations. Surfactant stabilizes the dispersion of particles (e.g., polymer particles, nanoparticles, etc.) and creates a molecular surface tension skin on the surface of the oil in order to reduce volatilization losses during use in an internal combustion engine.

Many mechanisms such as vehicles, tanks, aircraft, actuator screws, bearings, gauges, instruments, and other military equipment are required to perform well at very low temperatures (e.g., −75° C.). Lubricants, therefore, should perform well at low temperatures for such mechanisms. Among the properties of interest, the surfactants should have oxidation resistance, good extreme pressure antiwear properties, superior pliability, and excellent stability at ambient, as well as very low, temperatures. Although promising, the use of synthetic surfactants still remains limited due to production costs, thus making the bio-surfactant approach a better way to overcome the limitations.

Surface-active glycolipids, such as sophorolipids, are typically made from fatty acid and carbohydrate, using a selected number of yeast. The structural differences among the sophorolipids affect their specific physicochemical behavior, and their commercial success is mainly attributed to their substantial productivity and substrate conversion. A sophorolipid is typically a complex mixture of at least two glycolipids: the lactone form, which is hardly water soluble and has low foaming property; and the acid form, which is highly water soluble with high(er) foaming when compared to the lactone form. Properties, such as foaming, depend strongly (but not only) on ratio of lactone to acid form. In spite of their numerous advantages over the synthetic chemical surfactants, issues related with the large scale and cost-effective production still remain a major hurdle in economic competitiveness.

Therefore, there remains a need for cost-efficient bio-surfactants production with improved surfactant properties (e.g., high corrosion inhibition performance; good surface tension reduction). Particularly, there is a need for new and improved glycolipid compositions that are efficient and cost advantageous bio-surfactants having improved lubricant properties for high-temperature applications or low-temperature applications, improved surface-tension properties, and enhanced inhibition corrosion efficiency.

References for citing in an Information Disclosure Statement (37 C.F.R. 1.97(h)): U.S. Pub. No. 2015/0300139; U.S. Pub. No. 2015/0336999; U.S. Pub. No. 2016/0237334; E.P. 0550280B1; E.P. 3330341A1; E.P. 1411111B1; U.S. Pat. No. 9,683,164; N. Baccile, et al. "Development of a Cradle-to-Grave Approach for Acetylated Acidic Sophorolipid Biosurfactants" *ACS Sustainable Chemistry & Engineering*, 2017, 5, pp 1186-1198; E. I. P. Delbeke, et al. "Chapter 14—Sophorolipid Modification: The Power of Yeasts and Enzymes" Lipid Modification by Enzymes and Engineered Microbes, Edited by Bornscheuer UT: AOCS Press, 2018, pp 315-341; I. N. A. Van Bogaert, et al. "Microbial synthesis of sophorolipids" *Process Biochemistry*, 2011, 46, pp 821-833; I. N. A. Van Bogaert, et al. "Microbial production and application of sophorolipids" *Applied Microbiology and Biotechnology*, 2007, 76, pp 23-34; H. Wang, et al. "*Starmerella bombicola*: recent advances on sophorolipid production and prospects of waste stream utilization" *J. Chem. Technol. Biotechnol.*, 2019, 94, pp 999-1007; P. Ratsep, et al. "Identification and quantification of sophorolipid analogs using ultra-fast liquid chromatography-mass spectrometry" *Journal of Microbiological Methods*, 2009, 78, pp 354-356; J. D. Desai, et al. "Microbial Production of Surfactants and Their Commercial Potential" Microbiol. Bio. Rev., 1997, 61, pp 47-64; K. Ciesielskaa, et al. "Exoproteome analysis of *Starmerella bombicola* results in the discovery of an esterase required for lactonization of sophorolipids" *Journal of Proteomics*, 2014, 98, pp 159-174; M. J. Karen, et al. "One-Step Production of Unacetylated Sophorolipids by an Acetyltransferase Negative *Candida bombicola*" Biotechnology and Bioengineering, 2011, Vol. 108, No. 12; A. Koh, et al. "Effect of Sophorolipid n-Alkyl Ester Chain Length on Its Interfacial Properties at the Almond Oil-Water Interface" *Langmuir*, 2016, 32, pp 5562-5572; K. Hisatsuka, et al. "Formation of Protein-like Activator for n-Alkane Oxidation and Its Properties" *Agric. Biol. Chem.*, 1977, 41 (3), pp 445-450; S. Inoue, et al. "Sophorolipids from *Torulopsis bombicola* as microbial surfactants in alkane fermentation" *Biotechnology Letters*, 1982, 4, pp 3-8; U. Rau, et al. "Sophorolipids: a Source for Novel Compounds" *Industrial Crops and Products*, 2001, 13, pp 85-92; L. Zhang, et al. "Synthesis and interfacial properties of sophorolipid derivatives" *Colloids and Surfaces A: Physicochem. Eng. Aspects,* 2004, 240, pp 75-82; W. Gao, et al. "Glycolipid Polymer Synthesized from Natural Lactonic Sophorolipids by Ring Opening Metathesis Polymerization" *Macromolecules,* 2007, 40 (2), pp 145-147.

SUMMARY

The present disclosure relates to glycolipid compositions, methods for making glycolipid compositions, and uses thereof.

Glycolipid compositions can be prepared via yeast-mediated catalyzed reaction, and exhibit excellent surfactant properties having high corrosion inhibition performance, good reducing surface tension efficiency.

In at least one embodiment, a method for producing glycolipid compositions, such as sophorolipid compositions, includes contacting a feedstock including: (1) two or more $C_5$-$C_{50}$ monosaccharides and (2) a linear $C_3$-$C_{40}$ alpha-olefin, a branched $C_4$-$C_{40}$ alpha-olefin, a linear $C_4$-$C_{40}$ vinylidene, a branched $C_5$-$C_{40}$ vinylidene, a $C_1$-$C_{20}$ alcohol, or combination(s) thereof, with a yeast at a temperature of from about 20° C. to about 35° C., such as about 25° C.; and obtaining a glycolipid composition having a molecular weight of about 400 g/mol or greater.

Glycolipid compositions of the present disclosure can be glycolipid compositions comprising one or more lactonic glycolipids and one or more glycolipid acyclic esters. Processes of the present disclosure can provide glycolipid compositions having one or more of: a ratio of lactonic glycolipids to glycolipid acylic esters from about 1:10 to about 10:1; a lactonic glycolipid content of from about 15 wt % to about 85 wt %, based on the total weight of the glycolipid composition; a glycolipid acyclic ester content of from about 15 wt % to about 85 wt %, based on the total weight of the glycolipid composition; a molecular weight of from about 400 g/mol to about 10,000 g/mol; a corrosion rate of carbon steel from about 0.5 MPY to about 100 MPY at room temperature and at pH 4-6. In at least one embodiment, aqueous solutions of the glycolipid compositions of the present disclosure have a surface tension of from about 20 mN/m to about 80 mN/m.

DETAILED DESCRIPTION

Figure 1:
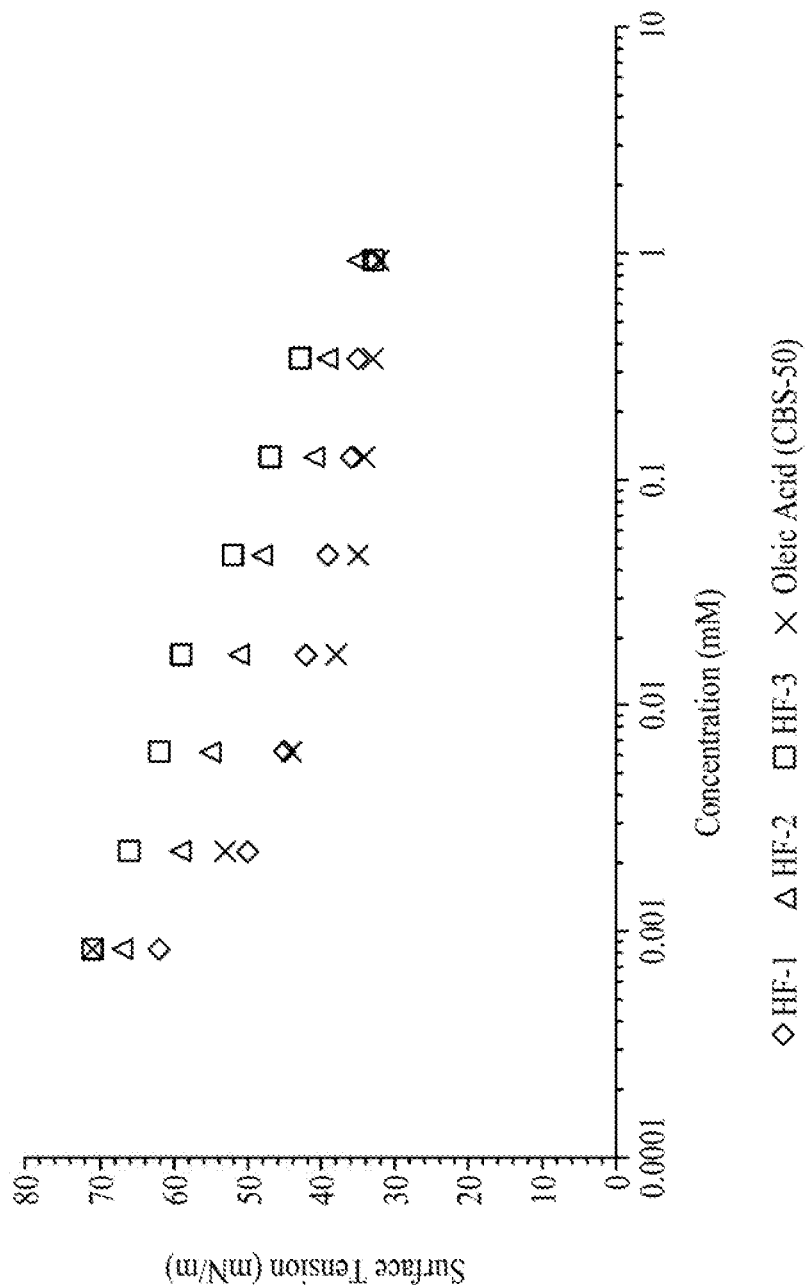
FIG. 1 is a graph illustrating the surface tension (mN/m) as a function of the concentration (mM) of the sophorolipid compositions, according to one embodiment.

The present disclosure relates to glycolipid compositions, methods for making glycolipid compositions, and uses thereof. Glycolipid compositions can have excellent surfactant properties such that the glycolipid compositions have high corrosion inhibition performance, good surface tension reduction, and improved lubricant properties for high-temperature and low-temperature applications, such as low-temperature applications.

A glycolipid composition may include: (1) one or more lactonic glycolipids having one or more linear $C_3$-$C_{40}$ alpha-olefin or branched $C_4$-$C_{40}$ alpha-olefin and one or more $C_{10}$-$C_{60}$ disaccharide; and (2) one or more glycolipid acyclic esters having one or more linear $C_3$-$C_{40}$ alpha-olefin or branched $C_4$-$C_{40}$ alpha-olefin and one or more $C_{10}$-$C_{60}$ disaccharide.

A glycolipid composition may include: (1) one or more lactonic glycolipids having one or more linear $C_4$-$C_{40}$ vinylidene or branched $C_5$-$C_{40}$ vinylidene and one or more $C_{10}$-$C_{60}$ disaccharide; and (2) one or more glycolipid acyclic esters having one or more linear $C_4$-$C_{40}$ vinylidene or branched $C_5$-$C_{40}$ vinylidene and one or more $C_{10}$-$C_{60}$ disaccharide.

A glycolipid composition may include (1) one or more lactonic glycolipids having one or more $C_1$-$C_{20}$ alcohol and one or more $C_{10}$-$C_{60}$ disacchardie; and (2) one or more glycolipid acyclic esters including one or more $C_1$-$C_{20}$ alcohol and one or more $C_{10}$-$C_{60}$ disaccharide.

A glycolipid composition may include: (1) one or more lactonic glycolipids having one or more linear $C_3$-$C_{40}$ alpha-olefin, branched $C_4$-$C_{40}$ alpha-olefin, linear $C_4$-$C_{40}$ vinylidene, branched $C_5$-$C_{40}$ vinylidene, $C_1$-$C_{20}$ alcohol, or a combination thereof and one or more $C_{10}$-$C_{60}$ disaccharide; and (2) one or more glycolipid acyclic esters having one or more linear $C_3$-$C_{40}$ alpha-olefin, branched $C_4$-$C_{40}$ alpha-olefin, linear $C_1$-$C_{40}$ vinylidene, branched $C_5$-$C_{40}$ vinylidene, $C_1$-$C_{20}$ alcohol, or a combination thereof and one or more $C_{10}$-$C_{60}$ disaccharide.

A glycolipid composition may include two or more glycolipids selected from the group consisting of:

(1) one or more lactonic glycolipids having one or more linear $C_3$-$C_{40}$ alpha-olefin or branched $C_4$-$C_{40}$ alpha-olefin and one or more $C_{10}$-$C_{60}$ disaccharide;

(2) one or more glycolipid acyclic esters having one or more linear $C_3$-$C_{40}$ alpha-olefin or branched $C_4$-$C_{40}$ alpha-olefin and one or more $C_{10}$-$C_{60}$ disaccharide;

(3) one or more lactonic glycolipids having one or more linear $C_4$-$C_{40}$ vinylidene or branched $C_5$-$C_{40}$ vinylidene and one or more $C_{10}$-$C_{60}$ disaccharide;

(4) one or more glycolipid acyclic esters having one or more linear $C_4$-$C_{40}$ vinylidene or branched $C_5$-$C_{40}$ vinylidene and one or more $C_{10}$-$C_{60}$ disaccharide;

(5) one or more lactonic glycolipids having one or more $C_1$-$C_{20}$ alcohol and one or more $C_{10}$-$C_{60}$ disaccharide; and (6) one or more glycolipid acyclic esters including one or more $C_1$-$C_{20}$ alcohol and one or more $C_{10}$-$C_{60}$ disaccharide.

A glycolipid composition may include a lactonic glycolipid content of from about 15 wt % to about 85 wt % (based on the total weight of the glycolipid composition), a glycolipid acyclic ester content of from about 15 wt % to about 85 wt % (based on the total weight of the glycolipid composition), at a ratio of lactonic glycolipids to glycolipid acylic esters from about 1:10 to about 10:1, and/or have a molecular weight of from about 400 g/mol to about 10,000 g/mol. A method for forming a glycolipid composition may include: introducing a population of a yeast to air and a first medium comprising one or more nitrogen source and one or more $C_{10}$-$C_{60}$ disaccharide to form a first culture. The method can include introducing at least a portion of the first culture to air and a feedstock in a second medium comprising one or more nitrogen source to form a second culture including the one or more glycolipid compositions, where the feedstock includes (1) one or more $C_{10}$-$C_{60}$ disaccharide and (2) one or more $C_1$-$C_{20}$ alcohol, linear $C_3$-$C_{40}$ alpha-olefin, branched $C_4$-$C_{40}$ alpha-olefin, linear $C_4$-$C_{40}$ vinylidene, branched $C_5$-$C_{40}$ vinylidene, or mixture(s) thereof. The method may include obtaining a glycolipid composition having a ratio of lactonic glycolipids to glycolipid acylic esters from about 1:10 to about 10:1, and having a molecular weight of from about 400 g/mol to about 10,000 g/mol.

Glycolipid compositions can be prepared via yeast-mediated catalyzed reactions, and exhibit excellent surfactant properties having high corrosion inhibition performance and/or good surface tension reduction.

In at least one embodiment, a method for producing glycolipid compositions, such as sophorolipid compositions, includes contacting a feedstock including: (1) two or more $C_5$-$C_{30}$ monosaccharide (such as a $C_5$-$C_6$ monosaccharide) and (2) linear $C_3$-$C_{40}$ alpha-olefin, branched $C_4$-$C_{40}$ alpha-olefin, linear $C_4$-$C_{40}$ vinylidene, branched $C_5$-$C_{40}$ vinylidene, $C_1$-$C_{20}$ alcohol, or combination(s) thereof, with a yeast (e.g., *Starmerella bombicola* ATCC 22214) at a temperature of from about 20° C. to about 35° C., such as about 25° C.; and obtaining a glycolipid composition having a molecular weight of about 400 g/mol or greater.

Glycolipid compositions of the present disclosure can be glycolipid compositions comprising one or more lactonic glycolipids and one or more glycolipid acyclic esters produced from a yeast (e.g., *Starmerella bombicola* ATCC 22214), in the presence of a nitrogen source. Processes of the present disclosure can provide glycolipid compositions having one or more of: a ratio of lactonic glycolipids to glycolipid acylic esters is from about 1:10 to about 10:1, a lactonic glycolipid content of from about 15 wt % to about 85 wt %, based on the total weight of the glycolipid composition, a glycolipid acyclic ester content of from about 15 wt % to about 85 wt %, based on the total weight of the glycolipid composition, a molecular weight of from about 400 g/mol to about 10,000 g/mol, a corrosion rate of carbon steel from about 0.5 MPY to about 100 MPY at room temperature and at pH 4-6. In at least one embodiment, an aqueous solutions of the glycolipid compositions of the present disclosure have a surface tension of from about 20 mN/m to about 80 mN/m.

The following abbreviations may be used herein: wt % is weight percent, mN/m is milliNewton per meter, VVM is Volume of air per Volume of culture per Minute, atm is atmosphere, rpm is rotation per minute, % (w/v) is percent weight/volume, L is liter, RT is room temperature (and is 23° C. unless otherwise indicated).

As used herein, an "olefin," alternatively referred to as "alkene," is a linear, branched, or cyclic compound of carbon and hydrogen having at least one double bond.

An "alpha-olefin", refers to an olefin having a terminal carbon-to-carbon double bond in the structure thereof $((R^xR^y)-C=CH_2$, where $R^x$ and $R^y$ can be independently hydrogen or any hydrocarbyl group, such as $R^x$ is hydrogen, and $R^y$ is an alkyl group). In other words, an "alpha-olefin" is an olefin having a double bond at the alpha (or 1-) position. A "linear alpha-olefin" is an alpha-olefin defined in this paragraph wherein $R^x$ is hydrogen, and $R^y$ is hydrogen or a linear alkyl group. A "linear alpha-olefin" or "LAO" is an olefin with a double bond at the alpha position and a linear hydrocarbon chain. For the purposes of this disclosure, the term "alpha-olefin" includes linear $C_3$-$C_{40}$ alpha-olefin, such as linear $C_{12}$-$C_{25}$ alpha-olefin, or branched $C_4$-$C_{40}$ alpha-olefin, such as branched $C_{12}$-$C_{25}$ alpha-olefin. Non-limiting examples of alpha-olefins include propylene, 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-methyl-1-pentene, 5-methyl-1-nonene, 3,5,5-trimethyl-1-hexene, 1-allyl-4-methylcyclohexane, vinylcyclohexane, and vinylnorbornane. Non-limiting examples of diolefins include 1,4-pentadiene, 1,5-hexadiene, 1,6-hexadiene, 1,7-octadiene, 1,8-nonadiene, 1,9-decadiene, 1,10-undecadiene, 1,11-dodecadiene, 1,3-divinylcyclopentane, 1,2-divinylcyclohexane, 1,3-divinylcyclohexane.

The term "alpha-olefin" includes vinylogous compounds. The term "vinyl" means an olefin having the following formula:

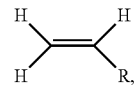

wherein R is a hydrocarbyl group, such as a saturated hydrocarbyl group.

The term "internal olefin" includes olefins that are vinylenes.

The term "linear olefins" includes 1,1-disubstituted olefins and linear internal olefins, such as 1,2-di-substituted olefins. The term "1,1-di-substituted olefin" includes "vinylidene". The term "vinylidene" means an olefin having the following formula:

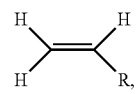

wherein each instance of R is independently a hydrocarbyl group, such as a saturated hydrocarbyl group.

The term "branched olefin" includes branched internal olefins such as "tri-substituted olefin". The term "tri-substituted olefin" includes tri-substituted vinylene. The term "tri-substituted vinylene" means an olefin having the following formula:

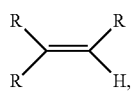

wherein each instance of R is independently a hydrocarbyl group, such as a saturated hydrocarbyl group.

The terms "hydrocarbyl radical," "hydrocarbyl group," or "hydrocarbyl" may be used interchangeably and are defined to mean a group consisting of hydrogen and carbon atoms only. For example, a hydrocarbyl can be a $C_1$-$C_{100}$ radical that may be linear, branched, or cyclic, and when cyclic, aromatic or non-aromatic. Examples of such radicals may include, but are not limited to, alkyl groups such as methyl, ethyl, n-propyl, isopropyl, n-butyl, isobutyl, sec-butyl, tert-butyl, pentyl, iso-amyl, hexyl, octyl cyclopropyl, cyclobutyl, cyclopentyl, cyclohexyl, cyclooctyl, and aryl groups, such as phenyl, benzyl naphthyl.

Unless otherwise indicated, (e.g., the definition of "substituted hydrocarbyl", "substituted aromatic", etc.), the term "substituted" means that at least one hydrogen atom has been replaced with at least one non-hydrogen group, such as a hydrocarbyl group, a heteroatom such as halogen (such as Br, Cl, F or I), or a heteroatom containing group, such as a carbonyl-containing group (such as an acetyl group), —$NR^*_2$, —$OR^*$, —$SeR^*$, —$TeR^*$, —$PR^*_2$, —$AsR^*_2$, —$SbR^*_2$, —$SR^*$, —$BR^*_2$, —$SiR^*_3$, —$GeR^*_3$, —$SnR^*_3$, —$PbR^*_3$, —$(CH_2)_q$—$SiR^*_3$, where q is 1 to 10 and each $R^*$ is independently a hydrocarbyl or halocarbyl radical, and two or more $R^*$ may join together to form a substituted or unsubstituted completely saturated, partially unsaturated, or aromatic cyclic or polycyclic ring structure), or where at least one heteroatom has been inserted within a hydrocarbyl ring.

The term "substituted hydrocarbyl" means a hydrocarbyl radical in which at least one hydrogen atom of the hydrocarbyl radical has been substituted with at least one heteroatom (such as halogen (e.g., Br, Cl, F or I) or heteroatom-containing group (such as a functional group, e.g., a carbonyl-containing group (such as an acetyl group), —$NR^*_2$, —$OR^*$, —$SeR^*$, —$TeR^*$, —$PR^*_2$, —$AsR^*_2$, —$SbR^*_2$, —$SR^*$, —$BR^*_2$, —$SiR^*_3$, —$GeR^*_3$, —$SnR^*_3$, —$PbR^*_3$, —$(CH_2)_q$—$SiR^*_3$, where q is 1 to 10 and each $R^*$ is independently a hydrocarbyl or halocarbyl radical, and two or more $R^*$ may join together to form a substituted or unsubstituted completely saturated, partially unsaturated, or aromatic cyclic or polycyclic ring structure), or where at least one heteroatom has been inserted within a hydrocarbyl ring.

Where isomers of a named alkyl (e.g., n-butyl, iso-butyl, and tert-butyl) reference to one member of the group (e.g., n-butyl) shall expressly disclose the remaining isomers (e.g., sec-butyl) in the family. Likewise, reference to an alkyl without specifying a particular isomer (e.g., butyl) expressly discloses all isomers (e.g., n-butyl, iso-butyl, sec-butyl, and tert-butyl).

For any particular compound disclosed herein, any general or specific structure presented also encompasses all conformational isomers, regio-isomers, and stereoisomers that may arise from a particular set of substituents, unless stated otherwise. Similarly, unless stated otherwise, the general or specific structure also encompasses all enantiomers, diastereomers, and other isomers whether in enantiomeric or racemic forms, as well as mixtures of stereoisomers.

The term "disaccharide" means any of a class of sugars, also referred to as "carbohydrates", whose molecules include two monosaccharide residues. In other words, a disaccharide is any of a group of sugars that yield two monosaccharide residues upon hydrolysis. Among the wide variety of disaccharides, three example disaccharides are sucrose, maltose, and lactose. Disaccharides have 12 carbon atoms, and their chemical formula is $C_{12}H_{22}O_{11}$. Other, less common disaccharides include lactulose, trehalose, chitobiose, and cellobiose. Disaccharides are formed through dehydration reactions in which a total of one water molecule is removed from the two monosaccharide residues. Another example of disaccharide is sophorose, which is included in sophorolipid structures, a surface-active glycolipid compound that can be synthesized by a selected number of yeast. Sophorose is a glycosylglucose that is D-glucose linked to a beta-D-glucopyranosyl unit at position 2 via a glycosidic linkage. It is one of the foremost parts of antibacterial, amphiphilic biosurfactant sophorolipid.

The term "monosaccharide" means a simple carbohydrate that consists of one sugar unit. The monosaccharides include simple sugars and their derivatives. They are the basic carbohydrate units from which more complex compounds can be formed. Monosaccharides include carbon, hydrogen, and oxygen atoms. When in their linear chain form, these molecules are polyhydroxylated aldehydes and ketones. The number of carbon atoms in monosaccharides varies from three to eight, but the most common number is five (e.g., pentoses, $C_5H_{10}O_5$) or six (e.g., hexoses, $C_6H_{12}O_6$). Monosaccharides do not yield smaller molecular weight sugars on hydrolysis. Monosaccharides can appear in either D- (dextro) or L- (levo) form, which are the mirror images of each other. Most naturally occurring monosaccharides are in the D-form and most synthetically produced are in the L-form. D- and L-forms have different properties. In aqueous solution, the linear chain form of a monosaccharide can convert into its corresponding two cyclic stereoisomer forms, also referred to as α- and β- "anomers". For purpose of the present disclosure, the monosaccharide may be a $C_5$-$C_{30}$ monosaccharide, such as substituted or unsubstituted 5-membered ring-monosaccharide (e.g., furanose, isomers and derivatives), or a substituted or unsubstituted 6-membered ring monosaccharide (e.g., pyranose, isomers and derivatives).

A "composition" of the present disclosure can include components (e.g., oil, glycolipids, etc.) and/or reaction product(s) of two or more of the components.

The term "continuous" means a system that operates without interruption or cessation. For example a continuous process to produce a glycolipid composition would be one where the reactants are continually introduced into one or more reactors and glycolipid composition product is continually withdrawn during a reaction process.

Glycolipid Compositions

The present disclosure relates to compositions of matter produced by the methods described herein.

In at least one embodiment, a process described herein produces glycolipid compositions having a molecular weight of 400 g/mol or greater.

In at least one embodiment, a glycolipid composition includes: (1) one or more lactonic glycolipids having one or more linear $C_3$-$C_{40}$ alpha-olefin or branched $C_4$-$C_{40}$ alpha-olefin and one or more $C_{10}$-$C_{60}$ disaccharide; and (2) one or more glycolipid acyclic esters having one or more linear $C_3$-$C_{40}$ alpha-olefin or branched $C_4$-$C_{40}$ alpha-olefin and one or more $C_{10}$-$C_{60}$ disaccharide. In at least one embodiment, the saccharide is sophorose and the glycolipid composition is a sophorolipid composition.

In alternate embodiments, a glycolipid composition includes: (1) one or more lactonic glycolipids having one or more linear $C_4$-$C_{40}$ vinylidene or branched $C_5$-$C_{40}$ vinylidene and one or more $C_{10}$-$C_{60}$ disaccharide; and (2) one or more glycolipid acyclic esters having one or more linear $C_4$-$C_{40}$ vinylidene or branched $C_5$-$C_{40}$ vinylidene and one or more $C_{10}$-$C_{60}$ disaccharide.

In alternate embodiments, a glycolipid composition includes: (1) one or more lactonic glycolipids having one or more $C_1$-$C_{20}$ alcohol and one or more $C_{10}$-$C_{60}$ disaccharide; and (2) one or more glycolipid acyclic esters including one or more $C_1$-$C_{20}$ alcohol and one or more $C_{10}$-$C_{60}$ disaccharide. In at least one embodiment, the saccharide is sophorose and the glycolipid composition is a sophorolipid composition.

In further embodiments, a glycolipid composition includes: (1) one or more lactonic glycolipids having one or more linear $C_3$-$C_{60}$ alpha-olefin, branched $C_4$-$C_{40}$ alpha-olefin, linear $C_1$-$C_{40}$ vinylidene, branched $C_5$-$C_{40}$ vinylidene, $C_1$-$C_{20}$ alcohol, or a combination thereof and one or more $C_{10}$-$C_{60}$ disaccharide; and (2) one or more glycolipid acyclic esters having one or more linear $C_3$-$C_{60}$ alpha-olefin, branched $C_4$-$C_{40}$ alpha-olefin, linear $C_4$-$C_{40}$ vinylidene, branched $C_5$-$C_{40}$ vinylidene, $C_1$-$C_{20}$ alcohol, or a combination thereof and one or more $C_{10}$-$C_{60}$ disaccharide.

In at least one embodiment, the saccharide is sophorose and the glycolipid composition is a sophorolipid composition.

A glycolipid composition may include two or more glycolipids selected from the group consisting of:

(1) one or more lactonic glycolipids having one or more linear $C_3$-$C_{40}$ alpha-olefin or branched $C_4$-$C_{40}$ alpha-olefin and one or more $C_{10}$-$C_{60}$ disaccharide;

(2) one or more glycolipid acyclic esters having one or more linear $C_3$-$C_{40}$ alpha-olefin or branched $C_4$-$C_{40}$ alpha-olefin and one or more $C_{10}$-$C_{60}$ disaccharide;

(3) one or more lactonic glycolipids having one or more linear $C_4$-$C_{40}$ vinylidene or branched $C_5$-$C_{40}$ vinylidene and one or more $C_{10}$-$C_{60}$ disaccharide;

(4) one or more glycolipid acyclic esters having one or more linear $C_4$-$C_{40}$ vinylidene or branched $C_5$-$C_{40}$ vinylidene and one or more $C_{10}$-$C_{60}$ disaccharide;

(5) one or more lactonic glycolipids having one or more $C_1$-$C_{20}$ alcohol and one or more $C_{10}$-$C_{60}$ disaccharide; and (6) one or more glycolipid acyclic esters including one or more $C_1$-$C_{20}$ alcohol and one or more $C_{10}$-$C_{60}$ disaccharide.

While the molecular weight of the glycolipid compositions produced herein can be influenced by reactor conditions including, for example, temperature, reactants concentration, yeast growth, reactional medium, and pressure, the glycolipid compositions produced by a process of the present disclosure may have a molecular weight of about 400 g/mol to about 10,000 g/mol, such as from about 500 g/mol to about 8,000 g/mol, such as from about 600 g/mol to about 6,000 g/mol, such as from about 800 g/mol to about 3,000 g/mol, such as from about 1,000 g/mol to about 2,000 g/mol, alternatively from about 2,500 g/mol to about 10,000 g/mol, as determined by Liquid Chromatography-Mass Spectrometry, also referred to as "LC-MS" (as described below).

In at least one embodiment, the glycolipid compositions are sophorolipid compositions having a molecular weight of about 400 g/mol to about 10,000 g/mol, such as from about 500 g/mol to about 8,000 g/mol, such as from about 600 g/mol to about 6,000 g/mol, such as from about 800 g/mol to about 3,000 g/mol, such as from about 1,000 g/mol to about 2,000 g/mol, alternatively from about 2,500 g/mol to about 10,000 g/mol, as determined by LC-MS.

In at least one embodiment, a glycolipid composition includes a lactonic glycolipid content of from about 15 wt % to about 85 wt %, such as from about 17.5 wt % to about 75 wt %, such as from about 20 wt % to about 50 wt %, alternatively from about 35 wt % to about 85 wt %, based on the total weight of the glycolipid composition.

In further embodiments, a glycolipid composition includes a glycolipid acyclic ester content of from about 15 wt % to about 85 wt %, such as from about 17.5 wt % to about 75 wt %, such as from about 20 wt % to about 50 wt %, alternatively from about 35 wt % to about 85 wt %, based on the total weight of the glycolipid composition.

In at least one embodiment, a glycolipid composition has a ratio of lactonic glycolipids to glycolipid acylic esters from about 1:10 to about 10:1, such as from about 1:7.5 to about 7.5:1, such as from about 1:5 to about 5:1, such as from about 1:2.5 to about 2.5:1.

In further embodiments, an aqueous solution having a glycolipid composition of the present disclosure has a surface tension in water (e.g., ultrapure water with a resistivity of 18 MΩ) of from about 20 mN/m to about 80 mN/m, such as from about 25 mN/m to about 75 mN/m, such as from about 30 mN/m to about 70 mN/m, such as from about 35 mN/m to about 65 mN/m, such as from about 40 mN/m to about 60 mN/m, alternatively from about 45 mN/m to about 80 mN/m, at a glycolipid composition concentration of 1 mM. Hence, glycolipid compositions of the present disclosure (e.g., sophorolipid compositions) exhibit good surfactant properties by lowering the surface tension, as compared to an aqueous solution without the glycolipid composition. For example, at a glycolipid composition concentration of 1 mM in ultrapure water (with a resistivity of 18 MΩ), an aqueous solution of a glycolipid composition of the present disclosure may have a surface tension of about 35 mN/m or less.

In at least one embodiment, glycolipid compositions of the present disclosure can exhibit anti-corrosion properties, such that when a metal (e.g., carbon steel) is treated with an acid (e.g., sweet carbon dioxide gas), the glycolipid compositions act as corrosion inhibitors. Accordingly, in the presence of the glycolipid compositions of the present disclosure, the corrosion rate of the metal treated with carbon dioxide gas (e.g., at a pressure of from about 0.05 bar to 3 bar, such as about 1 bar, for example), is from about 0.5 MPY to about 100 MPY, such as from about 1 MPY to about 50 MPY, such as from about 2 MPY to about 10 MPY, at pH value of about 4 to 6 (such as pH of 5), and at room temperature. For example, in the presence of a glycolipid composition of the present disclosure, the corrosion rate of carbon steel can be from about 0.5 MPY to about 10 MPY, such as from about 0.75 MPY to about 2 MPY at room temperature and at pH of about 4 to 6 (such as pH of 5). Furthermore, at pH value of 5 and at elevated temperature (e.g., temperature of about 30° C. to about 150° C., such as about 50° C. to 90° C.), the glycolipid compositions can exhibit a substantial corrosion inhibition performance such that the corrosion rate of a metal can be of from about 0.5 MPY to about 50 MPY, such as from about 0.75 MPY to about 20 MPY.

Non-limiting examples of metals may include iron, ferrous base metals, alloys of steel, alloys of nickel, coiled tubing, corrosion resistant alloys, or duplex steels. Alloys of steel can include stain less steel, chrome steel, martensitic alloy steel, ferritic alloy steel, carbon steel, precipitation-hardened stainless steels, or chromium.

Processes for Forming Glycolipid Compositions

Glycolipid compositions of the present disclosure can be prepared by fermentation of one or more feedstocks and a carbohydrate, with a yeast (e.g., *Starmerella bombicola* ATCC 22214) configured to produce glycolipids. The feedstock may include one or more $C_1$-$C_{20}$ alcohol, linear $C_3$-$C_{40}$ alpha-olefin, branched $C_4$-$C_{40}$ alpha-olefin, linear $C_4$-$C_{40}$ vinylidene, branched $C_5$-$C_{40}$ vinylidene, or a combination thereof. The glycolipid compositions can be used as a bio-surfactant, such as a low-foaming bio-surfactant, a low temperature lubricant, or a corrosion inhibitor. In at least one embodiment, the glycolipid compositions thus formed have improved surface tension properties, good lubricant properties for high-temperature and low-temperature applications, and enhanced inhibition corrosion efficiency, when compared to conventional synthetic surfactants or bio-surfactants. Furthermore, the glycolipid compositions can be used as a bio-surfactant configured to reduce surface tension if present in an aqueous solution.

In at least one embodiment, a process for the production of such glycolipid compositions includes: introducing a population of a yeast to air and a first medium comprising one or more nitrogen source and two or more $C_5$-$C_{30}$ monosaccharides (such as $C_5$-$C_6$ monosaccharides) (e.g., two monosaccharide monomers that are the same or different) to form a first culture. The method includes introducing at least a portion of the first culture to air and a feedstock in a second medium comprising one or more nitrogen source to form a second culture comprising the one or more glycolipid compositions, wherein the feedstock comprises (1) two or more $C_5$-$C_{30}$ monosaccharides and (2) a linear $C_3$-$C_{40}$ alpha-olefin or a branched $C_4$-$C_{40}$ alpha-olefin. The method optionally includes introducing one or more antibiotic to the first culture or the second culture. The method includes recovering the one or more glycolipid compositions from the second culture. The process for the production of the glycolipid compositions can be carried out in at least one solution reactor at a reactor pressure of from about 1 atm to about 3 atm (e.g., about 2 atm), a reactor temperature of from about 20° C. to about 35° C., and/or a pH of from about 3 to about 8, such as from about 3.5 to about 6, to form a glycolipid composition.

In at least one embodiment, a process for the production of such glycolipid compositions includes: introducing a population of yeast to air and a first medium comprising one or more nitrogen source and two or more $C_5$-$C_{30}$ monosaccharides (such as $C_5$-$C_6$ monosaccharides) (e.g., two monosaccharide monomers that are the same or different) to form a first culture. The method includes introducing at least a portion of the first culture to air and a feedstock in a second medium comprising one or more nitrogen source to form a second culture comprising the one or more glycolipid compositions, wherein the feedstock comprises (1) two or more $C_5$-$C_{30}$ monosaccharides and (2) a linear $C_5$-$C_{40}$ vinylidene or a branched $C_5$-$C_{40}$ vinylidene. The method optionally includes introducing one or more antibiotic to the first culture or the second culture. The method includes recovering the one or more glycolipid compositions from the second culture. The process for the production of the glycolipid compositions can be carried out in at least one solution reactor at a reactor pressure of from 1 atm to about 3 atm (e.g., about 2 atm), a reactor temperature of from about 20° C. to about 35° C., and/or a pH of from about 3 to about 8, such as from about 3.5 to about 6, to form a glycolipid composition.

In at least one embodiment, a process for the production of such glycolipid compositions includes: introducing a population of a yeast to air and a first medium comprising one or more nitrogen source and two or more $C_5$-$C_{30}$ monosaccharides (such as $C_5$-$C_6$ monosaccharides) (e.g., two monosaccharide monomers that are the same or different) to form a first culture. The method includes introducing at least a portion of the first culture to air and a feedstock in a second medium comprising one or more nitrogen source to form a second culture comprising the one or more glycolipid compositions, wherein the feedstock comprises (1) two or more $C_5$-$C_{30}$ monosaccharides and (2) a $C_1$-$C_{20}$ alcohol. The method includes introducing one or more antibiotic to the first culture or the second culture. The method includes recovering the one or more glycolipid compositions from the second culture. The process for the production of the glycolipid compositions can be carried out in at least one solution reactor at a reactor pressure of from 1 atm to about 3 atm (e.g., about 2 atm), a reactor temperature of from about 20° C. to about 35° C., and/or a pH of from about 3 to about 8, such as from about 3.5 to about 6, to form a glycolipid composition.

In at least one embodiment, a process for the production of such glycolipid compositions includes: introducing a population of a yeast to air and a first medium comprising one or more nitrogen source and two or more $C_1$-$C_{30}$ monosaccharides to form a first culture; introducing at least a portion of the first culture to air and a feedstock in a second medium comprising one or more nitrogen source to form a second culture comprising the one or more glycolipid compositions, wherein the feedstock comprises (1) two or more $C_5$-$C_{30}$ monosaccharide and (2) one or more $C_1$-$C_{20}$ alcohol, linear $C_3$-$C_{40}$ alpha-olefin, branched $C_{40}$ alpha-olefin, linear $C_4$-$C_{40}$ vinylidene, branched $C_5$-$C_{40}$ vinylidene, or a combination thereof. The method optionally includes introducing one or more antibiotic to the first culture or the second culture. The method includes recovering the one or more glycolipid compositions from the second culture. The process for the production of the glycolipid compositions can be carried out in at least one solution reactor at a reactor pressure of from 1 atm to about 3 atm (e.g., about 2 atm), a reactor temperature of from about 20° C. to about 35° C., and/or a pH of from about 3 to about 8, such as from about 3.5 to about 6, to form a glycolipid composition.

$C_1$-$C_{20}$ alcohol, linear $C_3$-$C_{40}$ alpha-olefin, branched $C_4$-$C_{40}$ alpha-olefin, linear $C_4$-$C_{40}$ vinylidene, branched $C_5$-$C_{40}$ vinylidene, or a mixture thereof, can be introduced to a processing reactor in a liquid state, and or in a gaseous state, or in a partially liquid-partially gaseous state.

The feedstock can be introduced at a flow rate of about 1 mL/min or less, such as from about 0.001 mL/min to about 1 mL/min, such as from about 0.01 mL/min to about 0.8 mL/min, such as from about 0.05 mL/min to about 0.6 mL/min, such as from about 0.1 mL/min to about 0.4 mL/min, alternatively from about 0.3 mL/min to about 1 mL/min. The reactor may have a working volume of from about 1 L to about 500,000 L.

The air can be introduced into the reactor at a flow rate of 0.25 VVM to about 2.5 VVM, such as from about 0.5 VVM to about 2 VVM, such as from about 0.75 VVM to about 1.75 VVM.

Formation of the first culture can be run at any temperature and or pressure suitable to obtain the desired first culture. Suitable temperatures and/or pressures may include a temperature from 20° C. to about 35° C., such as about 25° C. to about 30° C., such as about 23° C. to about 28° C., and/or at a pressure from about 1 atm to about 3 atm, such as from about 1.2 atm to about 2.8 atm, such as from about 1.4 atm to about 2.6, alternatively from about 1.5 atm to about 3 atm, alternatively at ambient pressure.

Formation of the second culture and production of the glycolipid compositions can be run at any temperature and or pressure suitable to obtain the desired first culture. Suitable temperatures and or pressures may include a temperature in the range of from 20° C. to about 35° C., such as about 25° C. to about 30° C., such as about 23° C. to about 28° C., and/or at a pressure from about 1 atm to about 3 atm, such as from about 1.2 atm to about 2.8 atm, such as from about 1.4 atm to about 2.6, alternatively from about 1.5 atm to about 3 atm, alternatively at ambient pressure.

The yeast cells can be cultured at a temperature of from 20° C. to about 35° C. (e.g., about 28° C.), with continuous agitation at about 150 rpm or greater, such as about 200 rpm or greater, such as about 225 rpm or greater, such as 250 rpm or greater, for a time period sufficient for the yeast cell growth and glycolipid compositions production and secretion, e.g., for about 1 hour to about 96 hours post inoculation with yeast cells, such as about 2 hours to about 72 hours, such as from about 4 hours to about 48 hours, such as from about 6 hours to about 24 hours, post inoculation with yeast cells, alternatively from about 24 hours to about 96 hours post inoculation with yeast cells. The yeast cells are further provided with a sufficient amount of a one or more feedstocks, e.g., as described above. In further embodiment, total yields of the glycolipid compositions are measured and determined after about 1 to 8 days growth. During and after growth in shake reactors, a hydrophobic liquid settles to the bottom of the growth reactor. The one or more glycolipid compositions secreted by the yeast cells have a density from about 1.00 g/mL to about 1.30 g/mL, such as from about 1.05 g/mL to about 1.25 g/mL, such as from about 1.10 g/mL to about 1.20 g/mL.

In at least one embodiment, a process for the production of glycolipid compositions includes maintaining the first culture and the second culture at a temperature of about 45° C. or less. The forming of the first culture can be performed for about 1 hour or greater. The forming of the second culture can be performed for about 24 hours or greater.

In at least one embodiment, a process for the production of a glycolipid composition includes isolating and/or purifying the one or more glycolipid compositions from the yeast culture. Without being bound by theory, it is believed that because the glycolipid compositions are extracellularly secreted from the yeast cells, and the yeast cell culture does not contain a hydrophobic carbon source, the one or more glycolipid compositions can be isolated and/or purified from the yeast cell culture without cell lysis or extraction requiring an organic solvent. The secreted glycolipid compositions are denser than water and can be recovered inexpensively using separation methods based on density such as centrifugation, continuous decanting, or simply letting the glycolipid composition settle to the bottom of a container. The glycolipid compositions, such as sophorolipid compositions, may be purified through hydrolysis and/or phase separation.

The yeast cells can be cultured under batch, fed-batch or continuous feed processing conditions. In varying embodiments, using batch, fed-batch or continuous feed cultivation conditions in which the culture can be repeatedly or continuously fed allowing the cells to continue producing the glycolipid compositions.

In at least one embodiment, the conversion of the feedstock is at least 5%, based upon glycolipid composition yield and the weight of the feedstock entering the reaction zone, such as 10% or more, such as 20% or more, such as 30% or more, such as 50% or more, such as 80% or more.

In further embodiments, the glycolipid compositions are produced at a yield of about 45% or greater, such as a yield range of from about 45% to about 95%, such as 50% to about 80%, based on the total weight of feedstock.

The nitrogen source may include nitrogen, peptones, yeast extract, meat extract, malt extract, corn steep liquor, soybean meal, urea and its derivatives, ammonia, ammonium salt (e.g., ammonium sulfate, ammonium chloride, ammonium phosphate, ammonium carbonate, ammonium nitrate), ammonium hydroxide, nitrate, nitrite, nucleotides, nucleosides, proteins, peptides, amino acids, or a mixture thereof. The first culture and the second culture may include about 0.05% (w/v) of nitrogen source, such as 0.1% (w/v) of nitrogen source. In at least one embodiment, the nitrogen source is a yeast extract, urea, or a mixture thereof.

The first culture and/or the second culture may include two or more $C_5$-$C_{30}$ monosaccharides (such as $C_5$-$C_6$ monosaccharides) at a concentration in the range of about 0.1% (w/v) (grams per 100 mL) to about 80% (w/v), such as about 0.25% (w/v) to about 70% (w/v), such as about 0.5% (w/v) to about 60% (w/v), such as about 1% (w/v) to about 50% (w/v), such as about 10% (w/v) to about 40% (w/v). In at least one embodiment, the first culture and/or the second culture include a carbon to nitrogen molar ratio of about 5:1 to about 400:1, such as from about 10:1 to about 200:1, such as from about 20:1 to about 100:1, such as from about 25:1 to about 75:1, such as from about 30:1 to about 40:1, e.g., using a nitrogen source that can be consumed or utilized by the yeast cells.

Additives, such as antibiotics, may be optionally added to the first and/or the second culture during the process of the glycolipid compositions production, thus preventing any bacterial contamination. Examples of antibiotics can be kanamycin, ampicillin, or a mixture thereof.

Molecular weight is determined by using an LC-MS. An Ultra High Performance Liquid Chromatography (UHPLC) coupled with Quadruplole-Time of Flight Mass Spectrometry (QToF MS) system is used for the LC-MS analysis. An octadecyl (C18) bound silica phase column (50×2.1 mm, inside diameter) can be used at an injection volume of 1 μL. Reversed phase gradient elution can be run using 0.1% formic acid in methanol/water (5/95) and acetonitrile as mobile phase A and B, respectively. The gradient can be programed to change elution strength over time. Mobile phase B/A ratio changed from 20/80-50/50-90/10-20/80 in 0 min-10 min-15 min-15.1 min followed by 7 min of equilibration time at the initial mobile phase condition prior to next injection.

Feedstocks: $C_5$-$C_{30}$ Monosaccharide

In at least one embodiment, methods for producing glycolipid compositions include introducing the yeast to a feed including two or more $C_5$-$C_{30}$ monosaccharides (such as $C_5$-$C_6$ monosaccharides). In another embodiment, the feed includes disaccharides, such as $C_{10}$-$C_{60}$ disaccharides, having, for example, a glucose, a mannose, a fructose, or a combination thereof. The $C_{10}$-$C_{60}$ disaccharides may include one or more substituents, such as —C(=O)($C_1$-$C_{10}$), such as acetyl groups. For example, the disaccharide is a $C_{12}$-disaccharide including one or two acetyl groups.

The $C_5$-$C_{30}$ monosaccharides may include one or more substituents, such as —C(═O)($C_1$-$C_{10}$), such as acetyl groups, any suitable alkyl-, alkenyl-, aryl-substituents. The $C_5$-$C_{30}$ monosaccharides can be glucose, mannose, fructose, galactose, rhamnose, or a combination thereof. The C5-C30 monosaccharides may include one or more acetyl groups. In at least one embodiment, the monosaccharide is glucose. Accordingly, when the monosaccharide is glucose (or a disaccharide of glucose, such as 2-O-beta-D-Glucopyranosyl-alpha-D-glucose, also referred to as "sophorose"), the yeast cells (e.g., *Starmerella bombicola* ATCC 22214) produce glycolipid compositions that are sophorolipid compositions. Exemplary of disaccharides used for the production of glycolipid compositions of the present disclosure can be cellobiose, trehalose, or sophorose. In at least one embodiment, the monosaccharide is a $C_5$-monosaccharide or a $C_6$-monosaccharide.

Feedstocks: $C_1$-$C_{20}$ Alcohol

The $C_1$-$C_{20}$ alcohol of the present disclosure can be a substituted or unsubstituted $C_1$-$C_{20}$ alcohol. In at least one embodiment, the feed includes one or more $C_1$-$C_{20}$ alcohol selected from methanol, ethanol, 1-propanol, 1-butanol, 1-pentanol, 1-hexanol, 1-heptanol, 1-octanol, 1-nonanol, 1-decanol, 1-undecenol, 1-dodecenol, 1-tridecenol, 1-tetradecenol, 1-pentadecenol, 1-hexadecenol, 1-heptadecenol, 1-octadecenol, 1-nonadecenol, 1-eicosenol, and derivatives thereof. Exemplary $C_1$-$C_{20}$ alcohol may also include isobutyl alcohol, isopentyl alcohol, isohexyl alcohol, isoheptyl alcohol, isooctyl alcohol, isononyl isodecyl alcohol, isoundecylalcohol, isododecyl alcohol, isotridecyl alcohol, propan-2-ol, 2-methyl-1-butanol. 2-ethyl-1-butanol, 2-propyl-1-butanol, 2-butyl-1-butanol 2,3-diethyl-1-pentanol, 2,3,4-trimethyl-1-pentadecenol, hydrocarbyl substituted-eicosenol, and derivatives thereof, and isomers thereof. In at least one embodiment, the $C_1$-$C_{20}$ alcohol is isoundecyl alcohol.

Feedstocks: Linear $C_3$-$C_{40}$ alpha-olefin, Branched $C_4$-$C_{40}$ alpha-olefin An alpha-olefin of the present disclosure can be a linear $C_3$-$C_{40}$ alpha-olefin or branched $C_4$-$C_{40}$ alpha-olefin, such as linear $C_{12}$-$C_{25}$ alpha-olefin or branched $C_{12}$-$C_{25}$ alpha-olefin. Alpha-olefins can include substituted or unsubstituted linear $C_3$-$C_{40}$ alpha-olefin or branched $C_4$-$C_{40}$ alpha-olefin, such as substituted or unsubstituted linear $C_{12}$-$C_{25}$ alpha-olefin or branched $C_{12}$-$C_{25}$ alpha-olefin, such as substituted or unsubstituted linear $C_{15}$-$C_{20}$ alpha-olefin or branched $C_{15}$-$C_{20}$ alpha-olefin, 1-heptene, octene, nonene, decene, undecene, dodecene and isomers thereof. In at least one embodiment, a substituted and or unsubstituted alpha-olefin is selected from one or more of 1-butene, 1-pentene, 1-hexene, 1-heptene, 1-octene, 1-nonene, 1-decene. In at least one embodiment, the feed comprises one or more linear $C_4$-$C_{40}$ alpha-olefins, such as one or more linear C12-C25 alpha-olefins, selected from 1-propene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, and isomers thereof. The feed may include one or more branched $C_4$-$C_{40}$ alpha-olefins, such as one or more branched $C_{12}$-$C_{25}$ alpha-olefins, selected from 3,4,5,-trimethyl-hept-1-ene, 4-methyl-dec-1-ene, 4-ethyl-2-methyl-dec-1-ene, 5-propyl-2-ethyl-undec-1-ene, dimer of 1-dodecene, dimer of 1-hexadecene, dimer of 1-octadecene, and derivatives thereof.

In at least one embodiment, the feed comprises dimers of linear $C_3$-$C_{40}$ alpha-olefin, dimers of branched $C_4$-$C_{40}$ alpha-olefin, or combination(s) thereof.

Feedstocks: Linear $C_4$-$C_{40}$ vinylidene, Branched $C_4$-$C_{40}$ vinylidene In at least one embodiment, the feed includes one or more linear $C_4$-$C_{40}$ vinylidene, such as one or more linear $C_{10}$-$C_{20}$ vinylidene. Exemplary linear $C_4$-$C_{40}$ vinylidene may include 3-methylenebutane, 3-methylenepentane, 3-methylenehexane, 3-methyleneheptane, 3-methyleneoctane, 3-methylenenonane, 3-methylenedecane, 3-methyleneundecane, 3-methylenedodecane, 3-methylenentridecane, 3-methylenetetradecane, 3-methylenepentadecane, 3-methylenehexadecane, 3-methyleneoctadecane, 3-methylenenonadecane, 4-methylenepentane, 4-methylenehexane, 4-methyleneheptane, 4-methyleneoctane, 4-methylenenonane, 4-methylenedecane, 4-methyleneundecane, 4-methylenedodecane, 4-methylenentridecane, 4-methylenetetradecane, 4-methylenepentadecane, 4-methylenehexadecane, 4-methyleneoctadecane, 4-methylenenonadecane, 5-methyleneheptane, 5-methyleneoctane, 5-methylenenonane, 5-methylenedecane, 5-methyleneundecane, 5-methylenedodecane, 5-methylenentridecane, 5-methylenetetradecane, 5-methylenepentadecane, 5-methylenehexadecane, 5-methyleneoctadecane, 5-methylenenonadecane, 6-methyleneoctane, 6-methylenenonane, 6-methylenedecane, 2-methyl-1-dodecene, 2-ethyl-1-dodecene, 2-propyl-1-dodecene, 2-butyl-1-dodecene, 2-pentyl-1-dodecene, 2-methyl-1-butene, 2,3-dimethyl-1-hexene, and derivatives thereof. Linear $C_4$-$C_{40}$ vinylidene can be selected from 9-methylenenonadecane, 2-methyl-1-dodecene, 2-ethyl-1-dodecene, 2-methyl-1-butene, and derivatives thereof.

The feed may include one or more branched $C_5$-$C_{40}$ vinylidene, such as one or more branched $C_{10}$-$C_{20}$ vinylidene. Exemplary branched $C_5$-$C_{10}$ vinylidene can be selected from 2-isobutyl-1-butene, 2,4-dimethyl-1-decene, 3,3-dimethyl-1-decene, and derivatives thereof.

In at least one embodiment, the feed comprises dimers of linear $C_4$-$C_{40}$ vinylidene, dimers of branched $C_5$-$C_{40}$ vinylidene, or combination(s) thereof.

Yeast

The yeast used for the production of the glycolipid compositions of the present disclosure can be any suitable yeast configured to produce glycolipids.

Yeast configured to produce glycolipids can include: *Starmerella bombicola* (also referred to as "*Candida bombicola*"), *Rhodotorula bogoriensis*, *Candida apicola*, *Pseudozyma antarctica*, *Pseudozyma aphidis*, *Ustilago maydis*, *Ustilago zeae*, *Pseudozyma flocculosa*, *Rhodococcus erythropolis*, *Pseudomonas aeruginosa*, *Pseudomonas* sp., *Rhodococcus erythropolis*, *Mycobacterium* sp., *Torulopsis bombicola*, *Torulopsis apicola*, *Torulospis petrophilum*, *Candida batistae*, *Candida floricola*, *Candida riodocensis*, *Candida rugosa*, *Candida kuoi*, *Candida stellata*, *Candida tropicalis*, *Cryptococcus* sp., *Cyberlindnera samutprakarnensis*, *Pichia anomala*, *Rhodotorula muciliginosa*, *Torulopsis gropengiesseri*, *Torulopsis petrophilum*, *Wickerhamiella domercqiae*, or mixture(s) thereof.

For example, *Starmerella bombicola* ATCC 22214 is a fungal/yeast which may be isolated from honey of bumblebees. *Starmerella bombicola* ATCC 22214 has important biotechnological potential, producing large amounts of biosurfactants, such as sophorolipids including fatty acids and sophorose. The population of *Starmerella bombicola* ATCC 22214 yeast cells is cultured in the yeast cell culture medium under conditions sufficient for yeast cell growth and glycolipid compositions production and secretion (as described above). The fermentation mode for *Starmerella bombicola* ATCC 22214 can be a submerged fermentation mode including batch and fed-batch strategies. In at least one embodiment, the yeast used for the production of glycolipid compositions (e.g., sophorolipid compositions) is *Starmerella bombicola* ATCC 22214.

End Uses

Among the various applications, the glycolipid compositions of the present disclosure can be used as a bio-surfactant (e.g., surface tension reducer), a lubricant (e.g., a low temperature lubricant), a low-foaming detergent, a corrosion inhibitor, an anti-bacterial agent, an anti-viral agent, an anti-fungal agent, a spermicide an insecticide, a cleanser, a detergent, a wetting agent, an antifoam agent, an emulsifier, an emollient, a dispersant, a humectant, an adhesive, a crystal modifier, an instantizer, a viscosity modifier, a mixing/blending aid, and/or a release agent. Glycolipid compositions of the present disclosure can also be used as base stocks useful in engine oils.

The term "low-foaming property" as used herein means a property showing a foaming power suitable for a washing process which involves a low-foaming property. The glycolipid compositions can exhibit a washing power which is equal to or better than the conventional low-foaming surfactants suitable for a washing process which involves the low-foaming property. Such property can be determined by performing a washing test using a soiled swatch, which is an evaluation method of washing power.

EMBODIMENTS LISTING

The present disclosure provides, among others, the following embodiments, each of which may be considered as optionally including any alternate embodiments.

Clause 1. A glycolipid composition comprising one or more lactonic glycolipids having one or more linear $C_3$-$C_{40}$ alpha-olefin or branched $C_4$-$C_{40}$ alpha-olefin, and one or more $C_{10}$-$C_{60}$ disaccharide; and one or more glycolipid acyclic esters having one or more linear $C_1$-$C_{40}$ alpha-olefin or branched $C_4$-$C_{40}$ alpha-olefin, and one or more $C_{10}$-$C_{60}$ disaccharide.

Clause 2. The glycolipid composition of Clause 1, wherein the one or more linear $C_3$-$C_{40}$ alpha-olefin is selected from 1-propene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, and derivatives thereof.

Clause 3. The glycolipid composition of Clauses 1 or 2, wherein the one or more linear $C_3$-$C_{40}$ alpha-olefin is selected from 1-dodecene, 1-hexadecene, and 1-octadecene.

Clause 4. The glycolipid composition of any of Clauses 1 to 3, wherein the one or more branched $C_4$-$C_{40}$ alpha-olefin is selected from 3,4,5,-trimethyl-hept-1-ene, 4-methyl-dec-1-ene, 4-ethyl-2-methyl-dec-1-ene, 5-propyl-2-ethyl-undec-1-ene, and derivatives thereof.

Clause 5. The glycolipid composition of any of Clauses 1 to 4, wherein the one or more $C_{10}$-$C_{60}$ disaccharide is a sophorose.

Clause 6. The glycolipid composition of any of Clauses 1 to 5, wherein the one or more $C_{10}$-$C_{60}$ disaccharide comprises one or more acetyl groups.

Clause 7. The glycolipid composition of any of Clauses 1 to 6, wherein the glycolipid composition comprises a sophorolipid.

Clause 8. The glycolipid composition of any of Clauses 1 to 7, wherein a ratio of lactonic glycolipids to glycolipid acylic esters is from about 1:10 to about 10:1.

Clause 9. The glycolipid composition of any of Clauses 1 to 8, wherein the glycolipid composition has a lactonic glycolipid content of from about 15 wt % to about 85 wt %, based on the total weight of the glycolipid composition.

Clause 10. The glycolipid composition of any of Clauses 1 to 9, wherein the glycolipid composition has a glycolipid acyclic ester content of from about 15 wt % to about 85 wt %, based on the total weight of the glycolipid composition.

Clause 11. The glycolipid composition of any of Clauses 1 to 10, wherein the glycolipid composition has a molecular weight of from about 400 g/mol to about 10,000 g/mol.

Clause 12. An aqueous composition comprising the glycolipid composition of any of Clauses 1 to 11, wherein the aqueous composition has a surface tension of from about 20 mN/m to about 80 mN/m at a glycolipid composition concentration range of 1 mM.

Clause 13. A carbon steel substrate comprising the glycolipid composition of any of Clauses 1 to 12 disposed thereon, wherein a corrosion rate of the carbon steel is from about 0.5 MPY to about 100 MPY at room temperature and at pH 4-6.

Clause 14. A glycolipid composition comprising one or more lactonic glycolipids having one or more linear $C_1$-$C_{40}$ vinylidene or branched $C_5$-$C_{40}$ vinylidene, and one or more $C_{10}$-$C_{60}$ disaccharide; and one or more glycolipid acyclic esters having one or more linear $C_4$-$C_{40}$ vinylidene or branched $C_4$-$C_{40}$ vinylidene, and one or more $C_{10}$-$C_{60}$ disaccharide.

Clause 15. The glycolipid composition of Clause 14, wherein the one or more linear $C_4$-$C_{40}$ vinylidene is selected from 9-methylenenonadecane, 2-methyl-1-dodecene, 2-ethyl-1-dodecene, 2-methyl-1-butene, and derivatives thereof.

Clause 16. The glycolipid composition of Clauses 14 or 15, wherein the one or more branched $C_4$-$C_{40}$ vinylidene is selected from 2-isobutyl-1-butene, 2,4-dimethyl-1-decene, 3,3-dimethyl-1-decene, and derivatives thereof.

Clause 17. The glycolipid composition of any of Clauses 14 to 16, wherein the one or more $C_{10}$-$C_{60}$ disaccharide is a sophorose.

Clause 18. The glycolipid composition of any of Clauses 14 to 17, wherein the $C_{10}$-$C_{60}$ disaccharide comprises one or more acetyl groups.

Clause 19. The glycolipid composition of any of Clauses 14 to 18, wherein the glycolipid composition comprises a sophorolipid.

Clause 20. The glycolipid composition of any of Clauses 14 to 19, wherein a ratio of lactonic glycolipids to glycolipid acyclic esters is from about 1:10 to about 10:1.

Clause 21. The glycolipid composition of any of Clauses 14 to 20, wherein the glycolipid composition has a lactonic glycolipid content of from about 15 wt % to about 85 wt %, based on the total weight of the glycolipid composition.

Clause 22. The glycolipid composition of any of Clauses 14 to 21, wherein the glycolipid composition has a glycolipid acyclic ester content of from about 15 wt % to about 85 wt %, based on the total weight of the glycolipid composition.

Clause 23. The glycolipid composition of any of Clauses 14 to 22, wherein glycolipid composition has a molecular weight of from about 400 g/mol to about 10,000 g/mol.

Clause 24. An aqueous composition comprising the glycolipid composition of any of Clauses 14 to 23, wherein the aqueous composition has a surface tension of from about 20 mN/m to about 70 mN/m at a glycolipid composition concentration range of 1 mM.

Clause 25. A carbon steel substrate comprising the glycolipid composition of any of Clauses 14 to 24 disposed thereon, wherein a corrosion rate of the carbon steel is from about 0.5 MPY to about 100 MPY at room temperature and at pH 4-6.

Clause 26. A glycolipid composition comprising one or more lactonic glycolipids having one or more $C_1$-$C_{20}$ alcohol, and one or more $C_{10}$-$C_{60}$ disaccharide; and one or more glycolipid acyclic esters comprising one or more $C_1$-$C_{20}$ alcohol, and one or more $C_{10}$-$C_{60}$ disaccharide.

Clause 27. The glycolipid composition of clause 26, wherein the one or more $C_{14}$-$C_{20}$ alcohol is selected from methanol, ethanol, 1-propanol, 1-butanol, 1-pentanol, 1-hexanol, 1-heptanol, 1-octanol, 1-nonanol, 1-decanol, 1-undecenol, 1-dodecenol, 1-tridecenol, 1-tetradecenol, 1-pentadecenol, 1-hexadecenol, 1-heptadecenol, 1-octadecenol, 1-nonadecenol, 1-eicosenol, and derivatives thereof.

Clause 28. The glycolipid composition of Clauses 26 or 27, wherein the one or more $C_{10}$-$C_{60}$ disaccharide is a sophorose.

Clause 29. The glycolipid composition of any of Clauses 26 to 28, wherein the one or more $C_{10}$-$C_{60}$ disaccharide comprises one or more acetyl groups.

Clause 30. The glycolipid composition of any of Clauses 26 to 29, wherein the glycolipid composition comprises a sophorolipid.

Clause 31. The glycolipid composition of any of Clauses 26 to 30, wherein a ratio of lactonic glycolipids to glycolipid acyclic esters is from about 1:10 to about 10:1.

Clause 32. The glycolipid composition of any of Clauses 26 to 31, wherein the glycolipid composition has a lactonic glycolipid content of from about 15 wt % to about 85 wt %, based on the total weight of the glycolipid composition.

Clause 33. The glycolipid composition of any of Clauses 26 to 32, wherein the glycolipid composition has a glycolipid acyclic ester content of from about 15 wt % to about 85 wt %, based on the total weight of the glycolipid composition.

Clause 34. The glycolipid composition of any of Clauses 26 to 33, wherein glycolipid composition has a molecular weight of from about 400 g/mol to about 5,000 g/mol.

Clause 35. An aqueous composition comprising the glycolipid composition of any of Clauses 26 to 34, wherein the aqueous composition has a surface tension of from about 20 mN/m to about 90 mN/m at a glycolipid composition concentration range of 1 mM.

Clause 36. A carbon steel substrate comprising the glycolipid composition of any of Clauses 26 to 35 disposed thereon, wherein a corrosion rate of the carbon steel is from about 0.5 MPY to about 100 MPY at room temperature and at pH 4-6.

Clause 37. A method for forming one or more glycolipid compositions in a reactor, the method comprising introducing a population of yeast to air and a first medium comprising one or more nitrogen source and one or more $C_{10}$-$C_{20}$ disaccharide to form a first culture; introducing at least a portion of the first culture to air and a feedstock in a second medium comprising one or more nitrogen source to form a second culture comprising the one or more glycolipid compositions, wherein the feedstock comprises (1) two or more $C_5$-$C_{30}$ monosaccharide and (2) one or more $C_1$-$C_{20}$ alcohol, linear $C_3$-$C_{40}$ alpha-olefin, branched $C_4$-$C_{40}$ alpha-olefin, linear $C_4$-$C_{40}$ vinylidene, or branched $C_5$-$C_{40}$ vinylidene; introducing one or more antibiotic to the first culture or the second culture; and recovering the one or more glycolipid compositions from the second culture.

Clause 38. The method of Clause 37, wherein the one or more glycolipid compositions comprises one or more lactonic glycolipids and one or more glycolipid acyclic esters.

Clause 39. The method of Clauses 37 or 38, wherein the ratio of lactonic glycolipids to glycolipid acyclic esters is from about 1:10 to about 10:1.

Clause 40. The method of any of Clauses 37 to 39, wherein the one or more nitrogen source is yeast extract or urea.

Clause 41. The method of any of Clauses 37 to 40, wherein the two or more $C_5$-$C_{30}$ monosaccharide comprise glucose, mannose, fructose, or a combination thereof.

Clause 42. The method of any of Clauses 37 to 41, wherein the two or more $C_5$-$C_{30}$ monosaccharide comprise one or more acetyl groups.

Clause 43. The method of any of Clauses 37 to 42, wherein the glycolipid composition comprises a sophorolipid.

Clause 44. The method of any of Clauses 37 to 43, wherein the feedstock comprises one or more linear C3-Cao alpha-olefins selected from 1-propene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, and derivatives thereof.

Clause 45. The method of any of Clauses 37 to 44, wherein the feedstock comprises one or more branched C4-Cao alpha-olefins selected from 3,4,5,-trimethyl-hept-1-ene, 4-methyl-dec-1-ene, 4-ethyl-2-methyl-dec-1-ene, 5-propyl-2-ethyl-undec-1-ene, dimer of 1-dodecene, dimer of 1-hexadecene, dimer of 1-octadecene, and derivatives thereof.

Clause 46. The method of any of Clauses 37 to 45, wherein the feedstock comprises one or more linear $C_4$-$C_{40}$ vinylidene selected from 9-methylenenonadecane, 2-methyl-1-dodecene, 2-ethyl-1-dodecene, 2-methyl-1-butene, and derivatives thereof.

Clause 47. The method of any of Clauses 37 to 46, wherein the feedstock comprises one or more branched $C_4$-$C_{30}$ vinylidene selected from 2-isobutyl-1-butene, 2,4-dimethyl-1-decene, 3,3-dimethyl-1-decene, and derivatives thereof.

Clause 48. The method of any of Clauses 37 to 47, wherein the feedstock comprises one or more $C_1$-$C_{20}$ alcohol selected from methanol, ethanol, 1-propanol, 1-butanol, 1-pentanol, 1-hexanol, 1-heptanol, 1-octanol, 1-nonanol, 1-decanol, 1-undecenol, 1-dodecenol, 1-tridecenol, 1-tetradecenol, 1-pentadecenol, 1-hexadecenol, 1-heptadecenol, 1-octadecenol, 1-nonadecenol, 1-eicosenol, and derivatives thereof.

Clause 49. The method of any of Clauses 37 to 48, further comprising maintaining the first culture and the second culture at a temperature of about 45° C. or less.

Clause 50. The method of any of Clauses 37 to 49, wherein forming the first culture is performed for about 1 hour or greater.

Clause 51. The method of any of Clauses 37 to 50, wherein forming the second culture is performed for about 24 hours or greater.

Clause 52. The method of any of Clauses 37 to 51, wherein the feedstock is introduced at a flow rate of about 1 mL/min or less.

Clause 53. The method of any of Clauses 37 to 52, wherein the reactor has a working volume of from about 1 L to about 500,000 L.

Clause 54. The method of any of Clauses 37 to 53, wherein the air is introduced at a flow rate of about 1 mL/min or less.

Clause 55. The method of any of Clauses 37 to 54, wherein the one or more glycolipid composition is used as a bio-surfactant, low temperature lubricant, or corrosion inhibitor.

Clause 56. The method of any of Clauses 37 to 55, wherein the bio-surfactant is a low-foaming bio-surfactant.

Clause 57. The method of any of Clauses 37 to 56, wherein the bio-surfactant is configured to reduce surface tension if present in an aqueous solution.

EXAMPLES

General Considerations: Reagents and Starting Materials

All reagents were purchased from Sigma-Aldrich, except for F-2 and F-3 which were made in ExxonMobil, instruments for analysis, etc. Surface tension measurements were taken on Kruss Force Tensiometer—K100.

NMR measurements were taken on Bruker 400 MHz NMR, Avance III.

Ultra High Performance Liquid Chromatography (UHPLC) coupled with Quadruplole-Time of Flight Mass Spectrometry (QToF MS) system was used for the LC-MS analysis. Samples were run on an octadecyl (C18) bound silica phase column (50×2.1 mm, i.d.) at an injection volume of 1 µL. Reversed phase gradient elution was run using 0.1% formic acid in methanol/water (5/95) and acetonitrile as mobile phase A and B, respectively. The gradient was programed to change elution strength over time. Mobile phase B/A ratio changed from 20/80-50/50-90/10-20/80 in 0 min-10 min-15 min-15.1 min followed by 7 min of equilibration time at the initial mobile phase condition prior to next injection.

Synthesis of Sophorolipid Compositions

The preparation of the sophorolipid compositions was carried out using the yeast strain Starmerella bombicola ATCC 22214 (S. bombicola) in a glucose/yeast extract/urea (GYU) medium. Feedstocks F-1 (e.g., a $C_{20}$-linear alpha olefin), F-2 (e.g., a $C_{20}$-vinyledene), and F-3 (e.g., a $C_{11}$-alcohol) were used as precursors of the sophorolipid compositions. Table 1 illustrates the GYU media composition. The pH was adjusted to 5.5-6.0 by using HCl before adding the feedstock. The autoclave was carried out at 115° C. for 20 min.

TABLE 1

| Component | Amount (g/L) |
|---|---|
| Glucose (2X) | 200 |
| Yeast extract | 10 |
| Urea | 1 |

Cultivation

A two phase fermentation was carried out (cell growth phase and sophorolipid production phase). The incubation of 50 mL cell culture in 250 mL baffled flasks was performed with rotary shaking at 250 rpm. For F-1, the cells growth was performed at 30° C. first, followed by the sophorolipid compositions production at 28° C. For F-2 and F-3, the cell growth was performed at 28° C. first, followed by the sophorolipid compositions production at 25° C.

Feed

The feedstock includes 10 ml of feedstock/50 ml cell culture.

Sophorolipid Compositions Precipitation Protocol Using F-1 as Feedstock

Colonies of S. bombicola from potato-dextrose agar plate were inoculated into 50 ml GYU media and grown at 30° C., 250 rpm, in a 250-mL baffled flask. After one day of cultivation, 1/10 diluted optical density (OD) 600 nm was 2.218. Five milliliter seed culture was inoculated in 50 mL fresh GYU media with 10 mL F-1 added. Antibiotics of 50 µg/mL kanamycin and 100 µg/mL ampicillin were added to the culture to prevent bacterial contamination. The inoculated culture was grown at 30° C. After about 30 hours of cultivation, the temperature was decreased to 28° C. and the culture was allowed to grow for another 7 days. After 7 days, 45 mL cell culture was heated up in a 50 mL falcon tube in an 80° C. oven for 30 min. Nearly 1.5 mL sophorolipid composition precipitated out to the bottom of the tube. The culture supernatant was removed by pipetting and sophorolipid composition was collected.

Sophorolipid Compositions Precipitation Protocol Using F-2 as Feedstock

Colonies of S. bombicola from potato-dextrose agar plate were inoculated into 50 ml GYU media and grown at 28° C., 250 rpm, in a 250-mL baffled flask. After one day of cultivation, 1/10 diluted OD 600 nm was 1.284. Five milliliter seed culture was inoculated in 50 mL fresh GYU media with 10 mL F-2 added. Antibiotics of 50 µg/mL kanamycin and 100 µg/mL ampicillin were added to the culture to prevent bacterial contamination. The inoculated culture was grown at 28° C. After about 30 hours, the temperature of the shaker was decreased to 25° C. and the culture was allowed to grow for another 7 days. After 7 days, the cultures were taken out of the shaker and kept at 4° C. After 3 days at 4° C., precipitation of the sophorolipid compositions could be seen for the culture with F-2 as the feedstock. The culture was centrifuged at 8,000 rpm for 15 min at 16° C., and the supernatant was removed by pipetting and the settled sophorolipid composition at the bottom of the tube was collected.

Sophorolipid Compositions Precipitation Protocol Using F-3 as Feedstock

Colonies of *S. bombicola* from potato-dextrose agar plate were inoculated into 50 ml GYU media and grown at 28° C., 250 rpm, in a 250-mL baffled flask. After one day of cultivation, 1/10 diluted OD 600 nm was 1.284. Five milliliter seed culture was inoculated in 50 mL fresh GYU media with 10 mL F-3 added. Antibiotics of 50 μg/mL kanamycin and 100 μg/mL ampicillin were added to the culture to prevent bacterial contamination. The inoculated culture was grown at 28° C. After about 30 hours, the temperature of the shaker was decreased to 25° C. and the culture was allowed to grow for another 7 days. After 7 days, the cultures were taken out of the shaker and kept at 4° C. 50 ml of F-3 was also centrifuged under same conditions as F-2 (e.g., the culture was centrifuged at 8,000 rpm for 15 min at 16° C.). The sophorolipid composition was dissolved in the top feedstock layer separated after centrifugation and was pipetted out.

TABLE 2

| Feed | Fraction |
|---|---|
| F-1 | Precipitated sophorolipid composition |
| F-2 | Precipitated sophorolipid composition |
| F-3 | Sophorolipid composition dissolved in feed |

The sophorolipid compositions yields were obtained in the range of 3 g-6 g after 3 days. The sophorolipid compositions were characterized by $^1$H-NMR and $^{13}$C-NMR, LC-MS and their surface tension in an aqueous solution and critical micelle concentrations were measured.

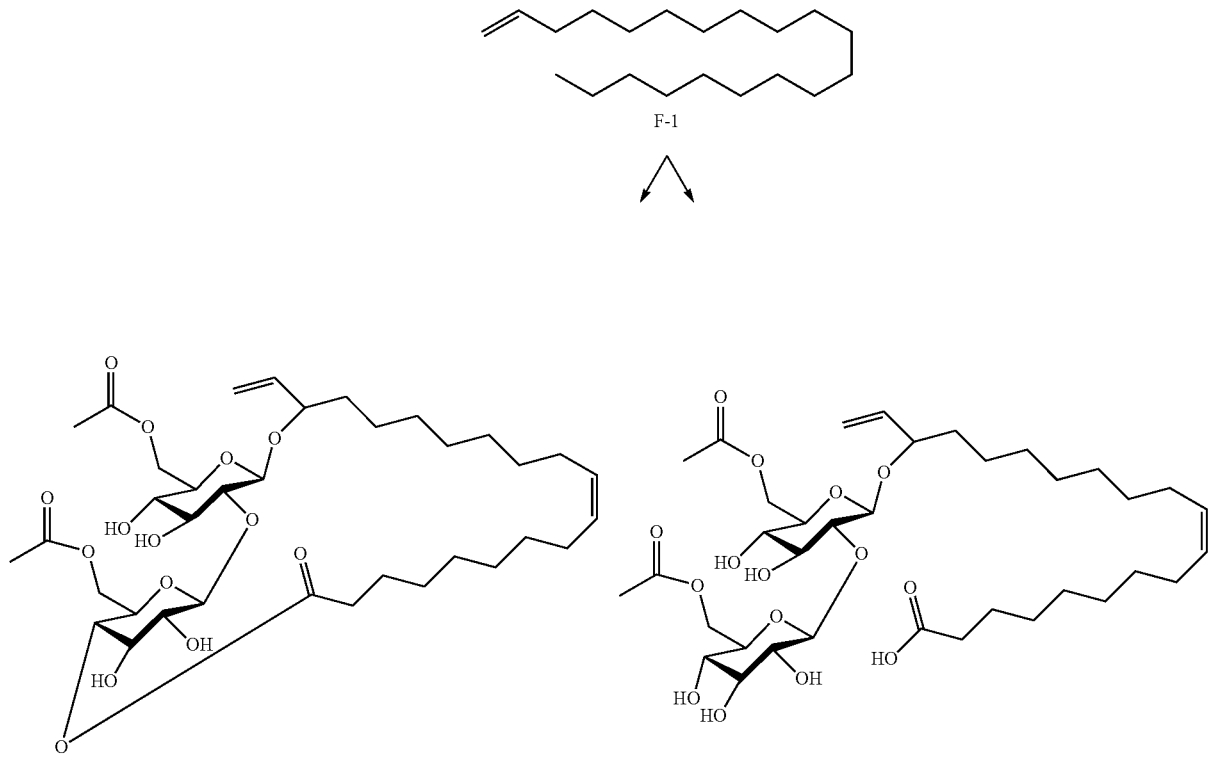

Scheme 1. Representative examples of petroleum derived sophorolipids

F-1

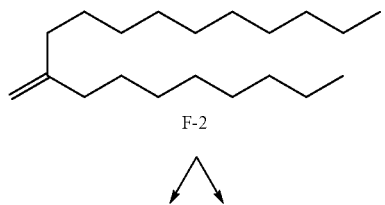

Scheme 2. Representative examples of petroleum derived sophorolipids

F-2

-continued

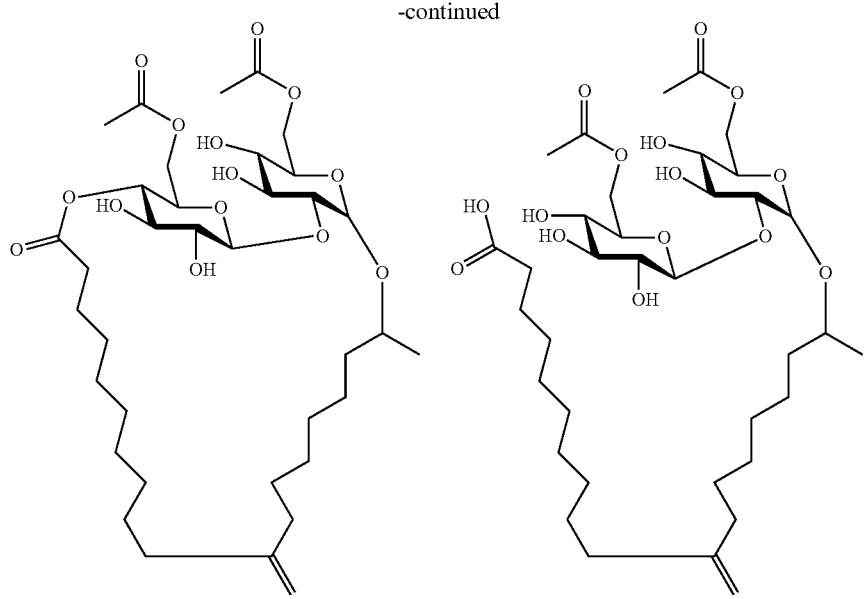

Scheme 3. Representative examples of petroleum derived sophorolipids

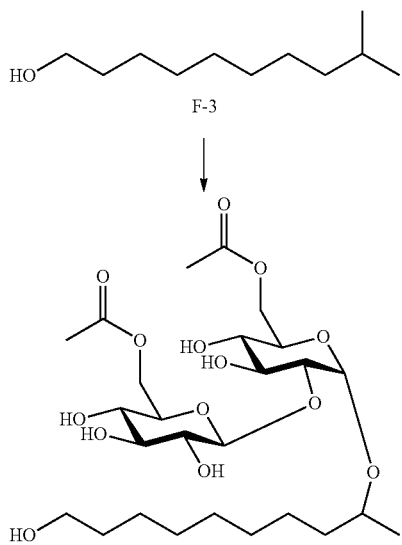

Surface Tension Measurements

The surface tension at different concentrations was determined using the plate method on Kruss Force Tensiometer—K100. Ultrapure water, 18 MΩ (60 mL) was placed in a glass dish. A stock solution of 0.03 mMol sophorolipid composition in ultrapure water was prepared in 100 mL volumetric flask. The following mole fractions were prepared by adding stock solution ln-18, ln-17, ln-16, ln-15, ln-14, ln-13, ln-12, and ln-11. "ln" refers to logarithmic scale. The surface tension was measured for each concentration. The commercial sample of oleic acid was used for reference (e.g., TensioGreen CBS-50).

Table 3 illustrates the surface tension (mN/m) of three different aqueous solutions of F-1, F-2, and F-3 derived sophorolipid compositions and is represented in FIG. 1 as a function of the concentration (mM) of the sophorolipid compositions.

TABLE 3

| In mole fraction (mol) | Concentration (mMol) | Surface Tension mN/m Substrate derived from | | | |
| --- | --- | --- | --- | --- | --- |
| | | F-1 | F-3 | F-2 | Oleic acid (TensioGreen CBS-50) |
| −18 | 8.43E−04 | 62 | 71 | 67 | 71 |
| −17 | 2.29E−03 | 50 | 66 | 59 | 53 |
| −16 | 6.23E−03 | 45 | 62 | 55 | 44 |
| −15 | 1.69E−02 | 42 | 59 | 51 | 38 |
| −14 | 4.60E−02 | 39 | 52 | 48 | 35 |
| −13 | 1.25E−01 | 36 | 47 | 41 | 34 |
| −12 | 3.40E−01 | 35 | 43 | 39 | 33 |
| −11 | 9.24E−01 | 33 | 33 | 35 | 32 |

Inhibition Corrosion Measurements

Figure 2:
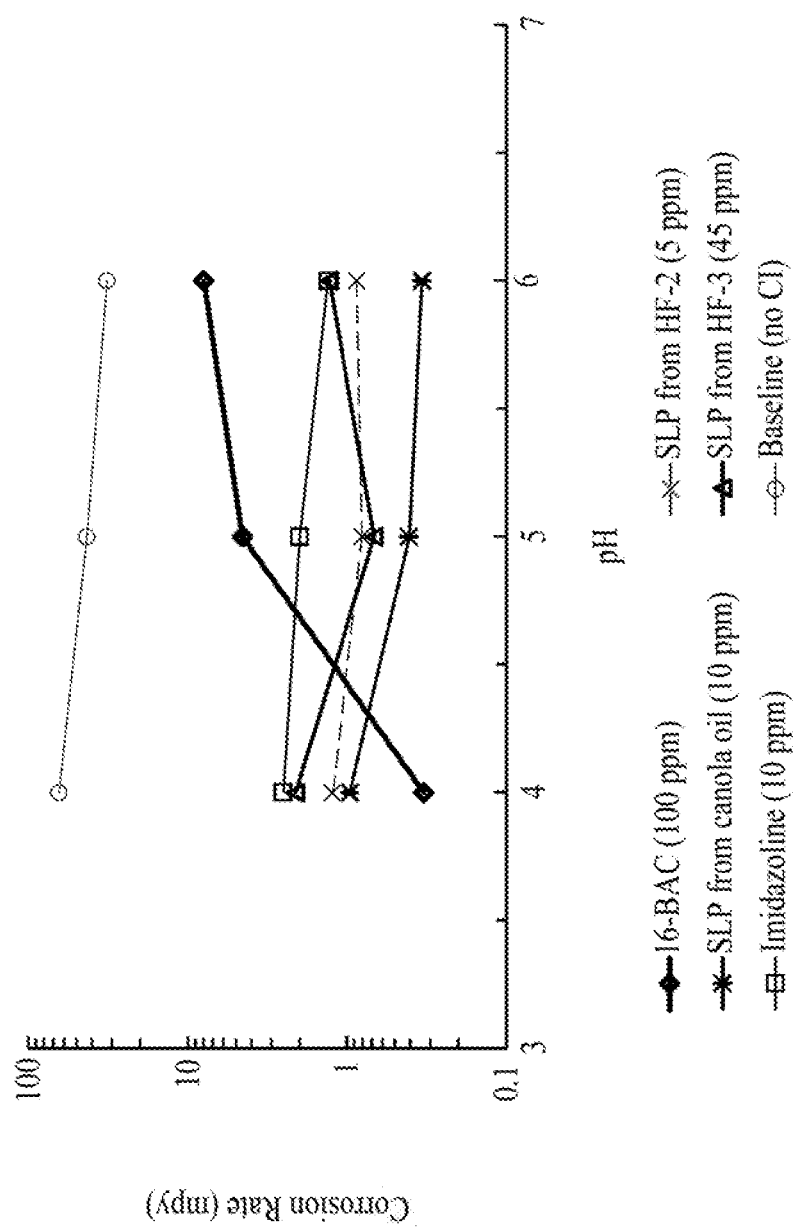
FIG. 2 is a graph illustrating a steady state corrosion rate of sophorolipid compositions as compared to conventional corrosion inhibitors, N-b-hydroxyethyl oleyl imidazoline and benzyldimethylhexadecylammonium chloride at different pH in 1 wt % NaCl solution at room temperature and 1 bar $CO_2$, according to one embodiment.
Figure 3:
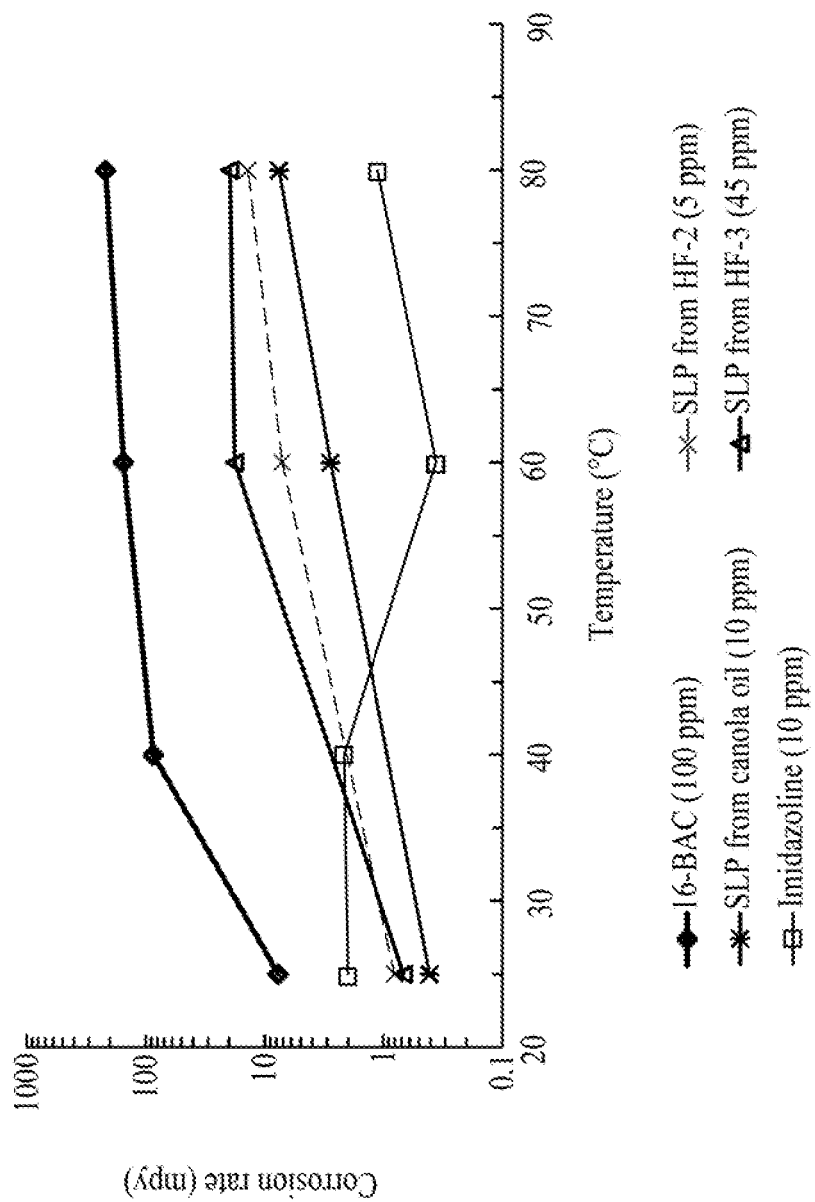
FIG. 3 is a graph illustrating a steady state corrosion rate of sophorolipid compositions as compared to conventional corrosion inhibitors, N-b-hydroxyethyl oleyl imidazoline and benzyldimethylhexadecylammonium chloride at different temperatures and pH=5, 1 wt % NaCl solution and 1 bar $CO_2$, according to one embodiment.

The corrosion inhibition performance of the sophorolipid composition-based surfactants as compared to conventional corrosion inhibitors, N-b-hydroxyethyl oleyl imidazoline (also referred to as "imidazoline") and benzyldimethylhexadecylammonium chloride (also referred to as "16-BAC"), in various $CO_2$ corrosion conditions were evaluated by electrochemical corrosion tests, and the results are shown in FIGS. 2 and 3. Corrosion tests were conducted in corrosion kettles filled with 1 wt % NaCl solution. The kettles were continuously purged with 1 bar $CO_2$, stirred with a magnetic bar rotating at a speed of 100 rpm, and the pH of the brine phase was adjusted to the targeted value using either sodium bicarbonate or hydrogen chloride. Electrochemical corrosion tests were undertaken using a standard three electrode arrangement, using a platinum wire as counter electrode, a saturated calomel electrode as the reference electrode, and a cylindrical working electrode made from X60 carbon steel. The selected concentration of the sophorolipid composition-based corrosion inhibitors was the minimum concentration required to achieve a steady state corrosion rate of X60 carbon steel below 4 mpy at pH=5 of the brine phase at room temperature, while the selected concentration for imidazoline and 16-BAC was the minimum concentration required to achieve the maximum inhibition efficiency of X60 carbon steel under the same conditions.

An approximately 3,000 mL brine solution was used in a cylindrical corrosion glass cell and stirred with a magnetic bar rotating at a speed of 100 rpm. The temperature in the cell was controlled by a stirring heater with a resistance temperature probe. A temperature variation of +/−1° C. to the targeted testing temperature was achieved. The inhibition corrosion measurements were conducted at atmospheric pressure. Prior to each measurement, the solution was purged with $N_2$ for 1 to 2 hours in order to deoxygenate, then $CO_2$ gas was bubbled into the solution for about 2 hours to ensure $CO_2$ saturation. The solution pH was then adjusted to the targeted pH by adding appropriate amount of either hydrogen chloride or sodium bicarbonate. The pH of the solution was monitored during the course of the measurement by a pH probe inserted into the cell, and a variation of +/−0.2 pH unit to the targeted pH was achieved for all the tests. The electrochemical corrosion measurements were undertaken using a standard three-electrode arrangement, using a platinum wire as counter electrode, a saturated calomel electrode (SCE) as the reference electrode, and a cylindrical working electrode made from X60 carbon steel. Before each tests, the working electrode (WE) was prepared by wet grinding to a 600-grit sand paper finish, rinsed with deionized (DI) water, methanol, and acetone, then blow dried with nitrogen gas. The dimensions of the electrode were then measured to accurately calculate the current density. A Gamry Reference 600™ potentiostat was used to conduct polarization resistance measurements at a 1 hour-time interval or 2 hour-time interval where the potential of the working electrode was varied from −10 mV to 10 mV of the corrosion potential (Ecorr) with a scan rate of 0.2 mV/s. Linear polarization resistance (LPR) (Rp, the slope of voltage/current close to Ecorr) was measured by Gamry Echem Analyst software at +/−5 mV with respect to Ecorr, and used to calculate the corrosion rate with an estimated B value of 0.026 V for $CO_2$ corrosion. The first hour was used to establish a baseline corrosion rate in the absence of any inhibitor. Following which, corrosion inhibitor was added and the measurement was continued for another 24 hours to 48 hours, or until a steady state corrosion rate was reached.

As shown in FIG. 2, HF-2 and HF-3 sophorolipid-based corrosion inhibitors showed superior corrosion inhibition performance to both imidazoline and 16-BAC at room temperature in the pH range of 4 to 6. At elevated temperatures and at pH=5 of the brine phase, the inhibition performance of sophorolipid composition-based corrosion inhibitions was comparable to the one of imidazoline, but enhanced sophorolipid composition-based corrosion inhibitions was observed when compared to 16-BAC's corrosion inhibition performance, as shown in FIG. 3.

Figure 4:
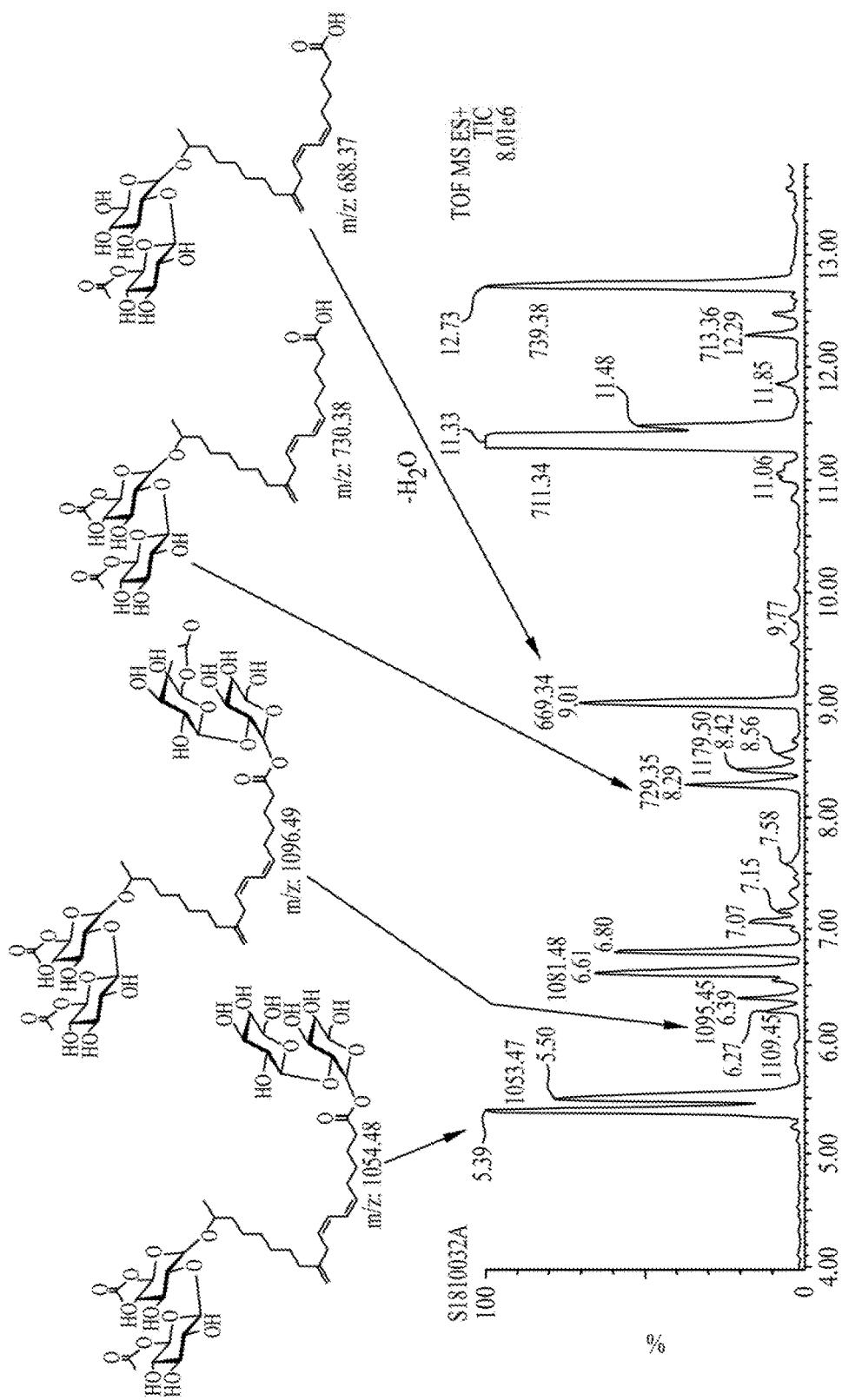
FIG. 4 illustrates an LC-MS spectrum of an HF-2-derived sophorolipid composition, according to one embodiment.
Figure 5:
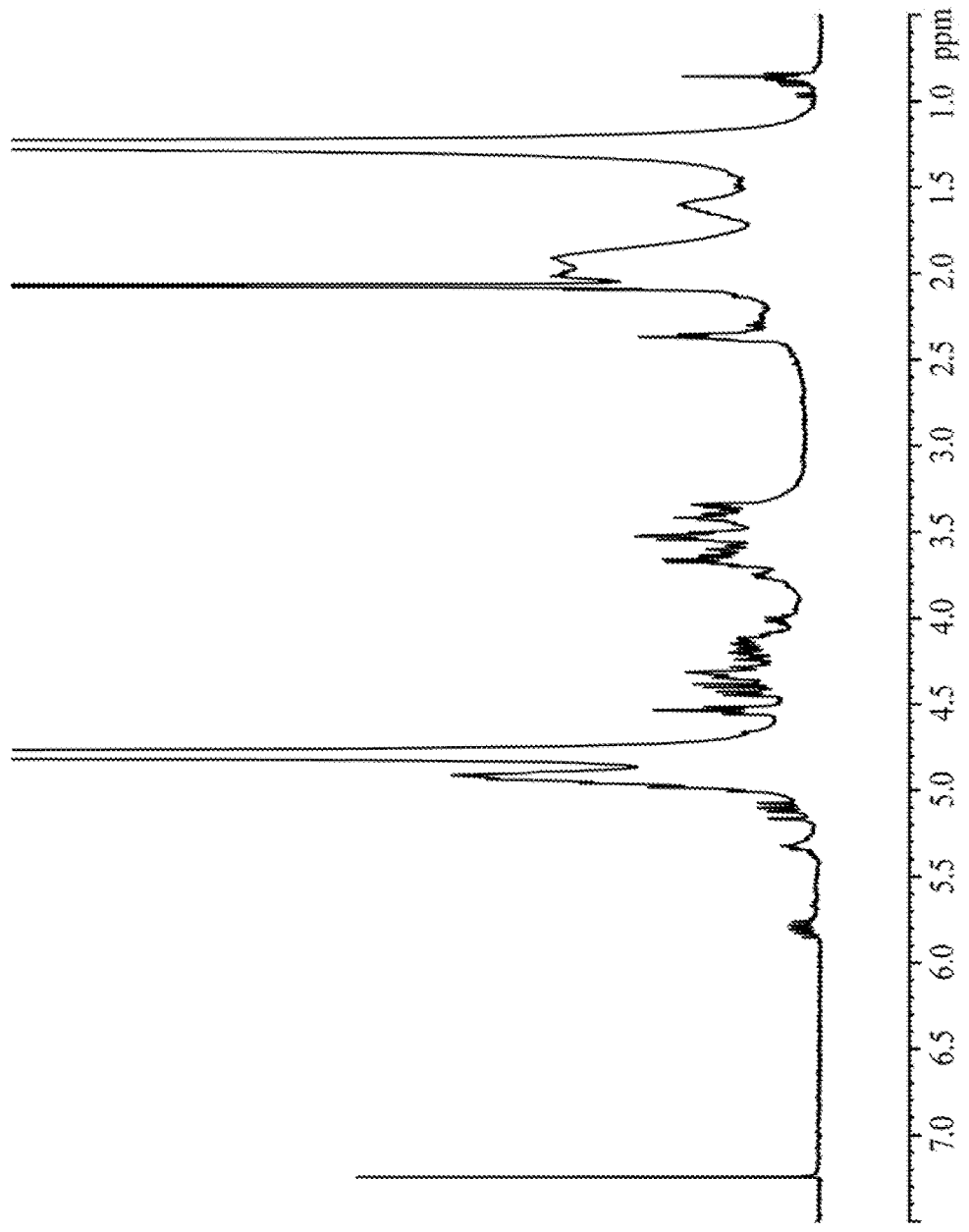
FIG. 5 illustrates a $^1$H-NMR spectrum of an HF-1-derived sophorolipid composition, according to one embodiment.
Figure 6:
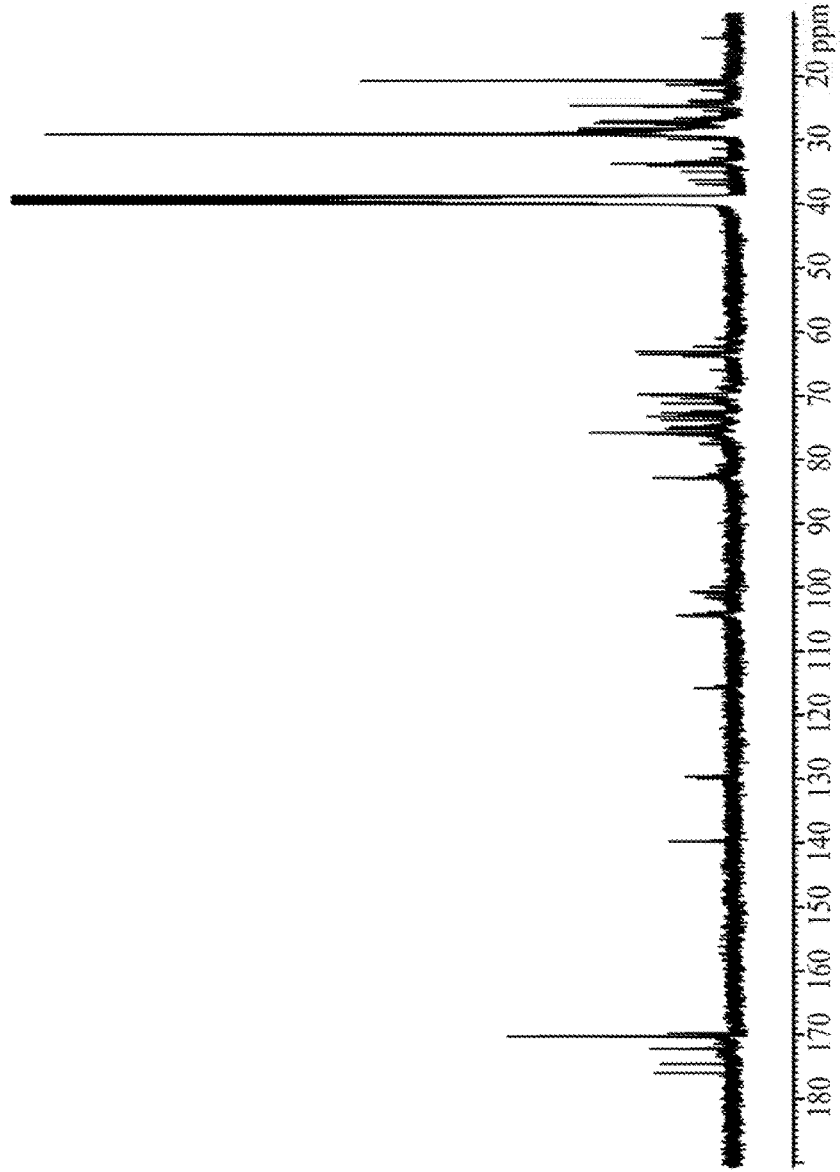
FIG. 6 illustrates a $^{13}$C-NMR spectrum of an HF-1-derived sophorolipid composition, according to one embodiment.
Figure 7:
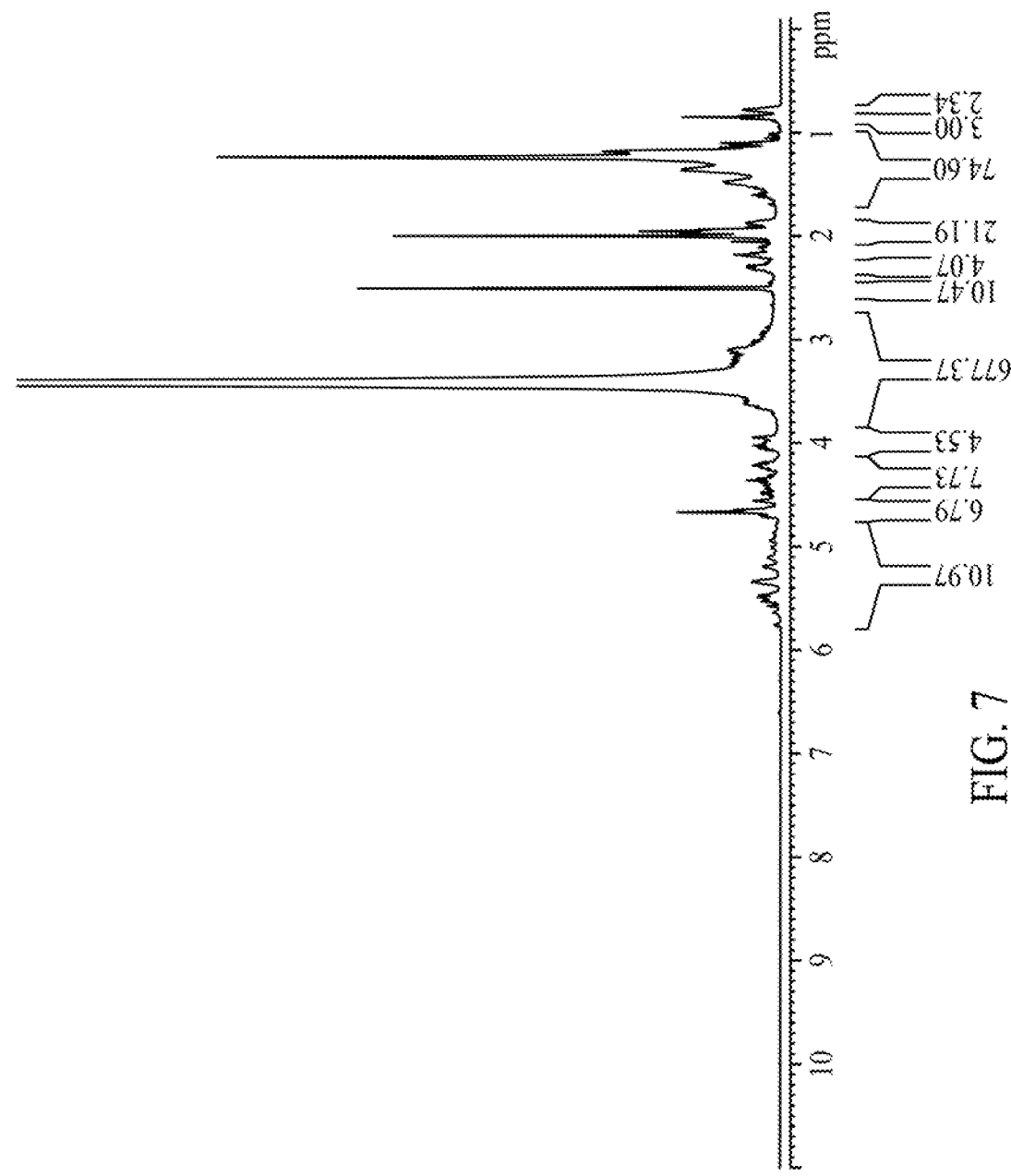
FIG. 7 illustrates a $^1$H-NMR spectrum of an HF-2-derived sophorolipid composition, according to one embodiment.
Figure 8:
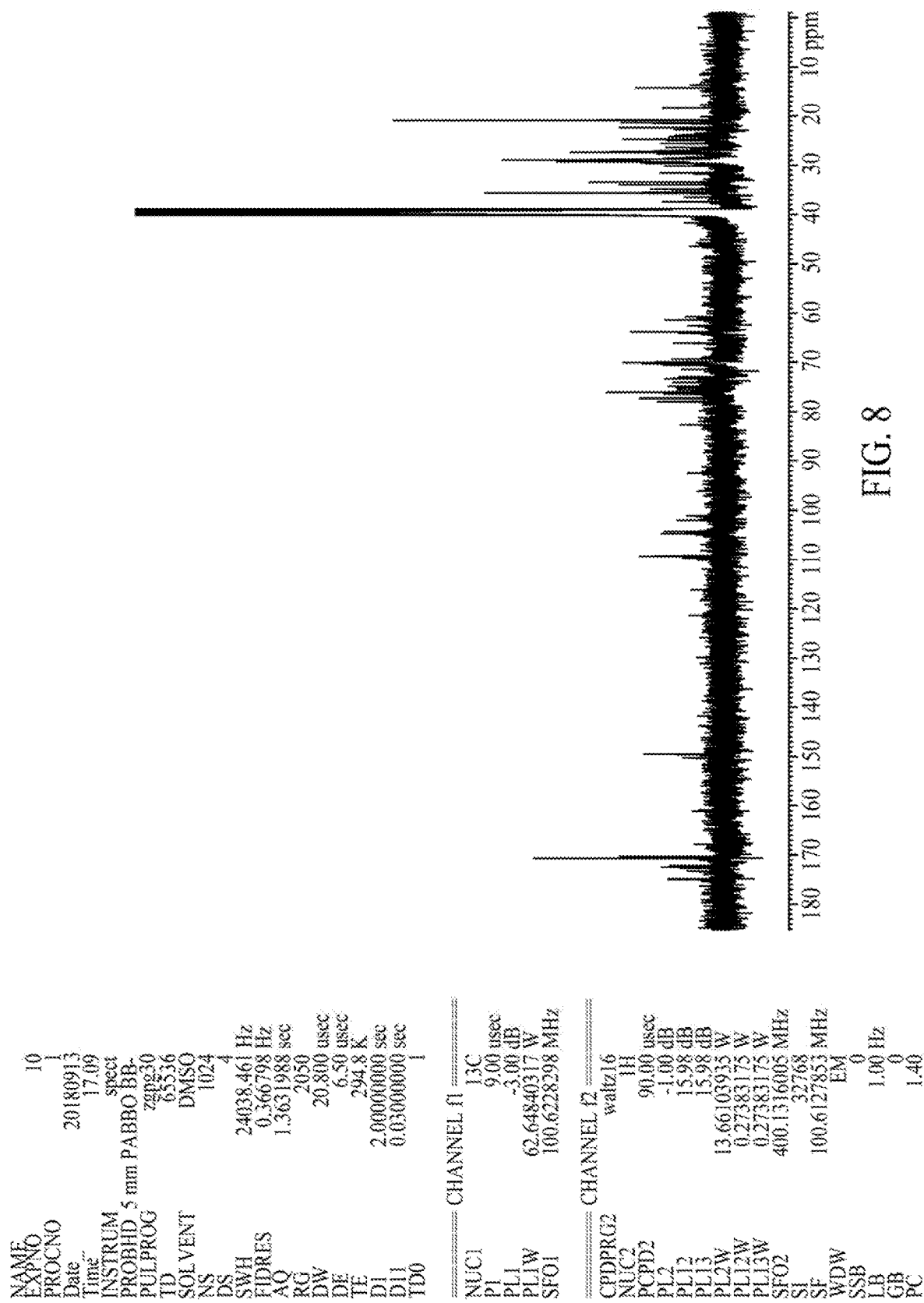
FIG. 8 illustrates a $^{13}$C-NMR spectrum of an HF-2-derived sophorolipid composition, according to one embodiment.
Figure 9:
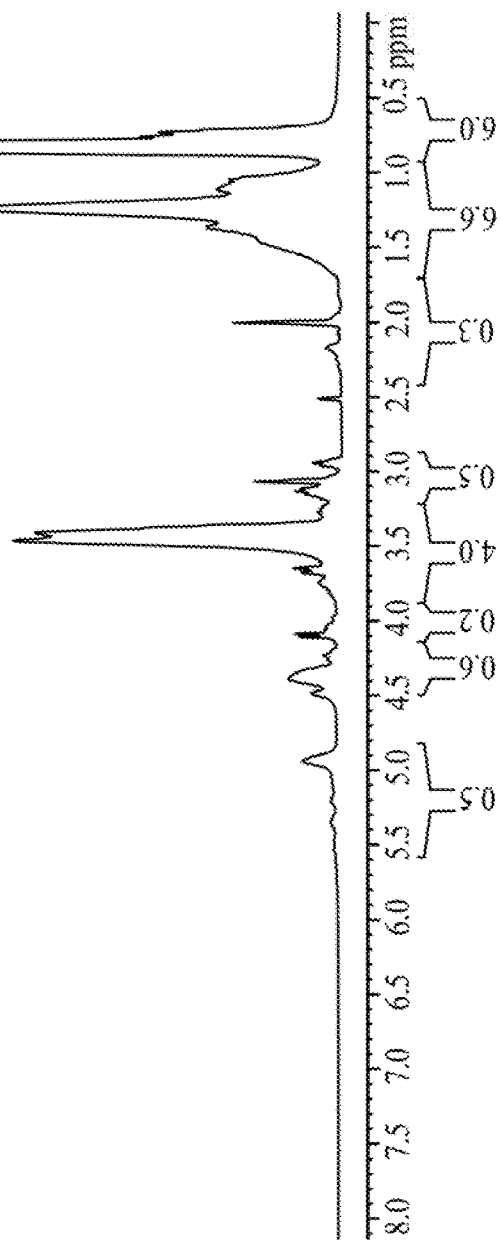
FIG. 9 illustrates a $^1$H-NMR spectrum of an HF-3-derived sophorolipid composition, according to one embodiment.
Figure 10:
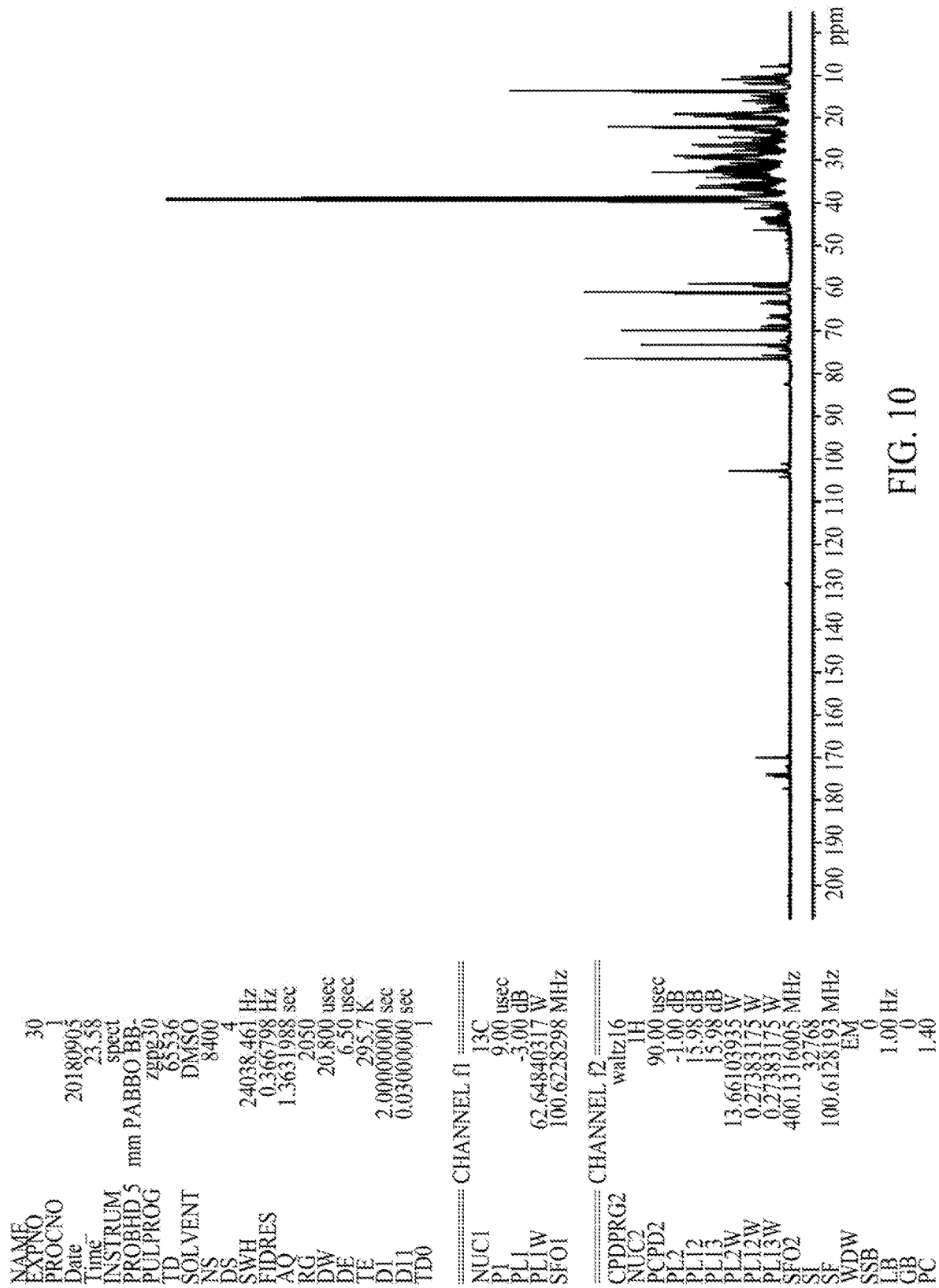
FIG. 10 illustrates a $^{13}$C-NMR spectrum of an HF-3-derived sophorolipid composition, according to one embodiment.

FIG. 4 illustrates an LC-MS spectrum of an F-2-derived sophorolipid composition, according to one embodiment. The F-2-derived sophorolipid composition includes sophorolipids having a molecular weight of from about 600 g/mol to about 1,200 g/mol. FIG. 5 illustrates a $^1$H-NMR spectrum of an F-1-derived sophorolipid composition, according to one embodiment. FIG. 6 illustrates a $^{13}$C-NMR spectrum of an F-1-derived sophorolipid composition, according to one embodiment. FIG. 7 illustrates a $^1$H-NMR spectrum of an F-2-derived sophorolipid composition, according to one embodiment. FIG. 8 illustrates a $^{13}$C-NMR spectrum of an F-2-derived sophorolipid composition, according to one embodiment. FIG. 9 illustrates a $^1$H-NMR spectrum of an F-3-derived sophorolipid composition, according to one embodiment. FIG. 10 illustrates a $^{13}$C-NMR spectrum of an F-3-derived sophorolipid composition, according to one embodiment.

Overall, the present disclosure provides glycolipid compositions, methods for making glycolipid compositions, and their uses thereof. Glycolipid compositions can be produced via yeast-mediated catalyzed reaction, from low cost petroleum-derived feeds with excellent bio-surfactant and corrosion inhibition properties, good surface tension reduction, and improved lubricant properties for high temperature and/or low-temperature applications.

The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of the present disclosure, additionally, they do not exclude impurities and variances normally associated with the elements and materials used.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

All documents described herein are incorporated by reference herein, including any priority documents and or testing procedures to the extent they are not inconsistent with this text. As is apparent from the foregoing general description and the specific embodiments, while forms of the present disclosure have been illustrated and described, various modifications can be made without departing from the spirit and scope of the present disclosure. Accordingly, it is not intended that the present disclosure be limited thereby. Likewise, the term "comprising" is considered synonymous with the term "including." Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

While the present disclosure has been described with respect to a number of embodiments and examples, those skilled in the art, having benefit of this disclosure, will appreciate that other embodiments can be devised which do not depart from the scope and spirit of the present disclosure.

What is claimed is:
1. A glycolipid composition comprising:
   one or more lactonic glycolipids having:
      one or more linear $C_3$-$C_{40}$ alpha-olefin or branched $C_4$-$C_{40}$ alpha-olefin, and
      one or more $C_{10}$-$C_{60}$ disaccharide; and one or more glycolipid acyclic esters having:
one or more linear $C_3$-$C_{40}$ alpha-olefin or branched $C_4$-$C_{40}$ alpha-olefin, and
one or more $C_{10}$-$C_{60}$ disaccharide;
wherein the one or more linear $C_3$-$C_{40}$ alpha-olefin is selected from the group consisting of 1-propene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, and 1-eicosene; and
wherein the one or more branched $C_4$-$C_{40}$ alpha-olefin is selected from the group consisting of 3,4,5,-trimethyl-hept-1-ene, 4-methyl-dec-1-ene, 4-ethyl-2-methyl-dec-1-ene, and 5-propyl-2-ethyl-undec-1-ene.

2. The glycolipid composition of claim 1, wherein the one or more $C_{10}$-$C_{60}$ disaccharide is a sophorose.

3. The glycolipid composition of claim 1, wherein the one or more $C_{10}$-$C_{60}$ disaccharide comprises one or more acetyl groups.

4. The glycolipid composition of claim 1, wherein the glycolipid composition has a molecular weight of from about 400 g/mol to about 10,000 g/mol.

5. A method for forming one or more glycolipid compositions in a reactor, the method comprising:
introducing a population of yeast to air and a first medium comprising one or more nitrogen source and one or more $C_{10}$-$C_{60}$ disaccharide to form a first culture;
introducing at least a portion of the first culture to air and a feedstock in a second medium comprising one or more nitrogen source to form a second culture comprising the one or more glycolipid compositions, wherein the feedstock comprises (1) two or more $C_5$-$C_{30}$ monosaccharide and (2) one or more linear $C_3$-$C_{40}$ alpha-olefin or branched $C_4$-$C_{40}$ alpha-olefin;
wherein the one or more linear $C_3$-$C_{40}$ alpha-olefin is selected from the group consisting of 1-propene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, and 1-eicosene; and
wherein the one or more branched $C_4$-$C_{40}$ alpha-olefin is selected from the group consisting of 3,4,5,-trimethyl-hept-1-ene, 4-methyl-dec-1-ene, 4-ethyl-2-methyl-dec-1-ene, 5-propyl-2-ethyl-undec-1-ene, dimer of 1-dodecene, dimer of 1-hexadecene, dimer of 1-octadecene; and
introducing one or more antibiotic to the first culture or the second culture; and
recovering the one or more glycolipid compositions from the second culture.

6. The method of claim 5, wherein the one or more glycolipid compositions comprises one or more lactonic glycolipids and one or more glycolipid acyclic esters.

7. The method of claim 5, wherein the two or more $C_5$-$C_{30}$ monosaccharides comprise glucose, mannose, fructose, or a combination thereof.

8. The method of claim 5, wherein the two or more $C_5$-$C_{30}$ monosaccharides comprise one or more acetyl groups.

9. The method of claim 5, further comprising maintaining the first culture and the second culture at a temperature of about 45° C. or less.

* * * * *